(12) United States Patent  (10) Patent No.:   US 7,914,804 B2
O'Neil et al.  (45) Date of Patent:   Mar. 29, 2011

(54) SLOW RELEASE PHARMACEUTICAL PREPARATION AND METHOD OF ADMINISTERING SAME

(75) Inventors: Alexander George B. O'Neil, Subiaco (AU); Yandi Liu, Willeton (AU)

(73) Assignee: Palmaya Pty Ltd, Subiaco (AU)

( * ) Notice: Subject to any disclaimer, the term of this patent is extended or adjusted under 35 U.S.C. 154(b) by 138 days.

(21) Appl. No.: 10/363,107

(22) PCT Filed: Sep. 3, 2001

(86) PCT No.: PCT/AU01/01107
§ 371 (c)(1),
(2), (4) Date: May 7, 2003

(87) PCT Pub. No.: WO02/17971
PCT Pub. Date: Mar. 7, 2002

(65) Prior Publication Data
US 2003/0170305 A1    Sep. 11, 2003

(51) Int. Cl.
A61F 13/00    (2006.01)
A61F 2/00    (2006.01)
A61K 9/20    (2006.01)
A61K 9/22    (2006.01)
A61K 9/14    (2006.01)

(52) U.S. Cl. ........ 424/422; 424/423; 424/426; 424/464; 424/468; 424/489

(58) Field of Classification Search .................. 424/489, 424/464; 427/212
See application file for complete search history.

(56) References Cited

U.S. PATENT DOCUMENTS 3,523,906 A    8/1970   Vrancken et al. ............. 252/316
(Continued)

FOREIGN PATENT DOCUMENTS

GB    1598458    9/1981
(Continued)

OTHER PUBLICATIONS

I. Soriano and C. Evora, "Formulation of calcium phosphates/poly (d,l-lactide) blends containing gentamicin for bone implantation," Journal of Controlled Release, Elsevier Science Publishers, B.V. (Amsterdam, The Netherlands), vol. 68 ( No. 1), p. 121-134, (Jul. 17, 2000).

(Continued)

*Primary Examiner* — Humera N Sheikh
(74) *Attorney, Agent, or Firm* — Fredrikson & Byron, P.A.

(57) ABSTRACT

A pharmaceutical preparation adopted for sustained release of an active agent(s) over an extended period of time at a therapeutic rate without an initial burst release of the agent(s) upon administration, wherein the preparation comprises: (i) an outer portion prepared from one or more layers of a biodegradable polymer, which is selected to release an active agent over an extended period of time when positioned in situ in a patient, and (ii) an inner portion comprising a plurality of micro-capsules formed from at least a biodegradable polymer, said micro capsules containing at least an active agent, wherein the micro-capsules are compressed into the form of a tablet under suitable pressure to suppress the rate of release of the active agent from the micro-capsules. The present specification also relates to a method for inserting one or more implants(s) into a tissue of a mammal comprising the following steps: a) making a small incision into the tissue with a needle and a first sheath; b) withdrawing the needle from the first sheath but leaving the first sheath in the tissue; c) dilating the opening of the incision by inserting a dilator and second sheath of larger diameter through the body of the first sheath; d) withdrawing the dilator from the second sheath, but leaving the second sheath in the tissue; e) disturbing the implant(s) from a sheath filled with implant(s) by inserting said sheath into the final sheath inserted into the tissue and pushing a dilator into the sheath thereby releasing said implant(s) into the tissue.

62 Claims, 23 Drawing Sheets

U.S. PATENT DOCUMENTS

| | | | | |
|---|---|---|---|---|
| 3,737,337 | A * | 6/1973 | Schnoring et al. | 427/212 |
| 4,351,337 | A * | 9/1982 | Sidman | |
| 5,183,464 | A | 2/1993 | Dubrul et al. | 128/3 |
| 5,304,119 | A | 4/1994 | Balaban et al. | 604/51 |
| 5,503,851 | A * | 4/1996 | Mank et al. | 424/489 |
| 5,817,343 | A | 10/1998 | Burke | |
| 6,203,813 | B1 * | 3/2001 | Gooberman | |

FOREIGN PATENT DOCUMENTS

| | | |
|---|---|---|
| GB | 2 103 927 | 3/1983 |
| WO | WO 97/27843 | 8/1997 |
| WO | WO 00/02616 | 1/2000 |

OTHER PUBLICATIONS

Schwope, A.D., et al., "Lactic/glycolic acid polymers as narcotic antagonist delivery systems," Life Sciences, vol. 17 ( No. 12), p. 1877-1885, (Nov. 17, 1975).

Harrigan, S.E., et al., "Pharmacological Evaluation of Narcotic Antagonist Delivery Systems in Rhesus Monkeys", NIDA Research Monograph, vol. 28, 1981, pp. 77-92.

Reuning, R.H. et al., "Pharmacokinetic Quantitation of Naltrexone Release From Several Sustained-Relsease Delivery Systems", NIDA Research Monograph, vol. 28, 1981, pp. 172-184.

* cited by examiner

Figure 5 Naltrexone levels in the blood plasma of rats are shown above

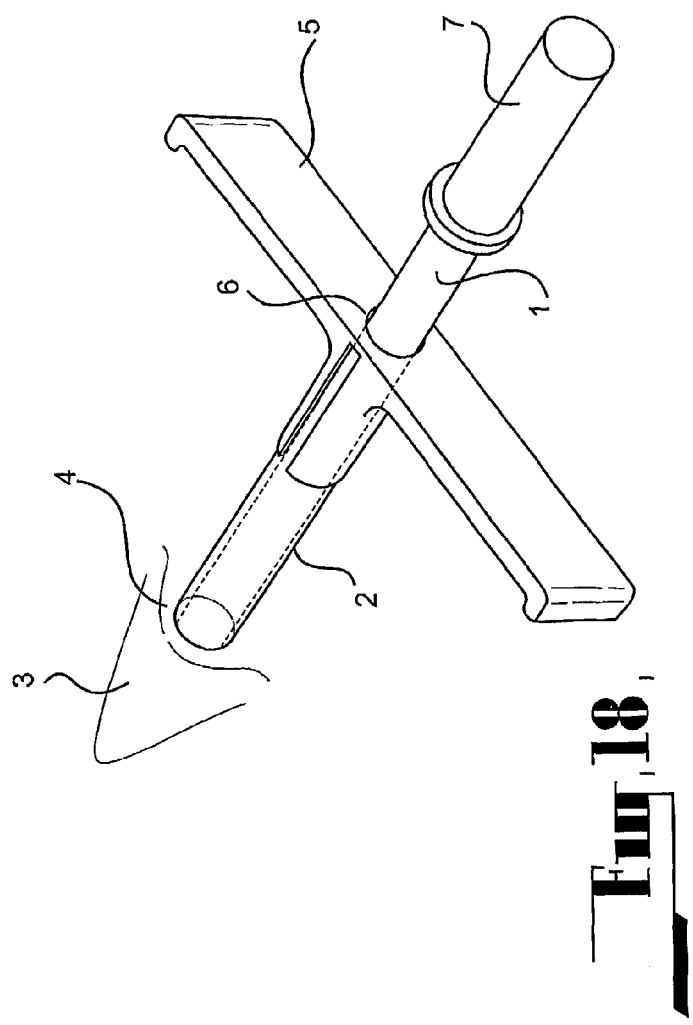
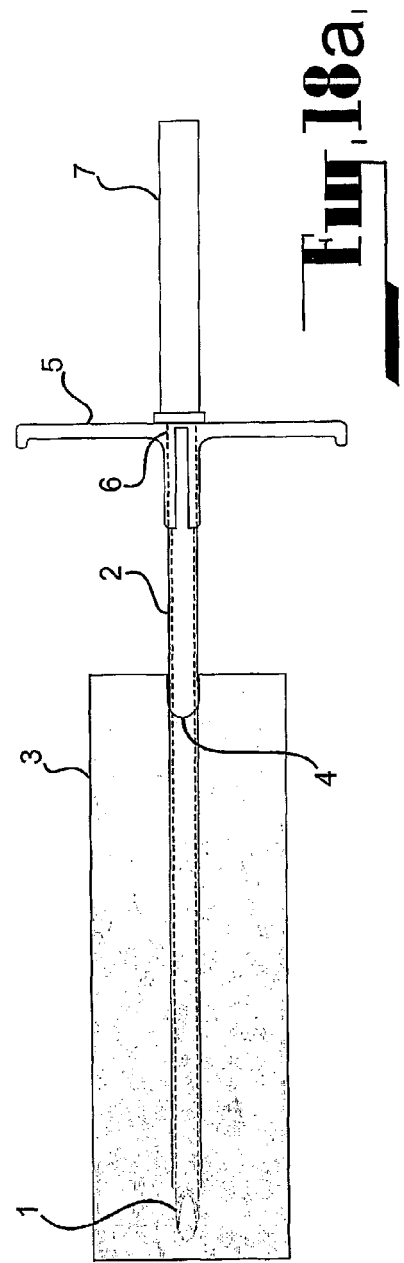

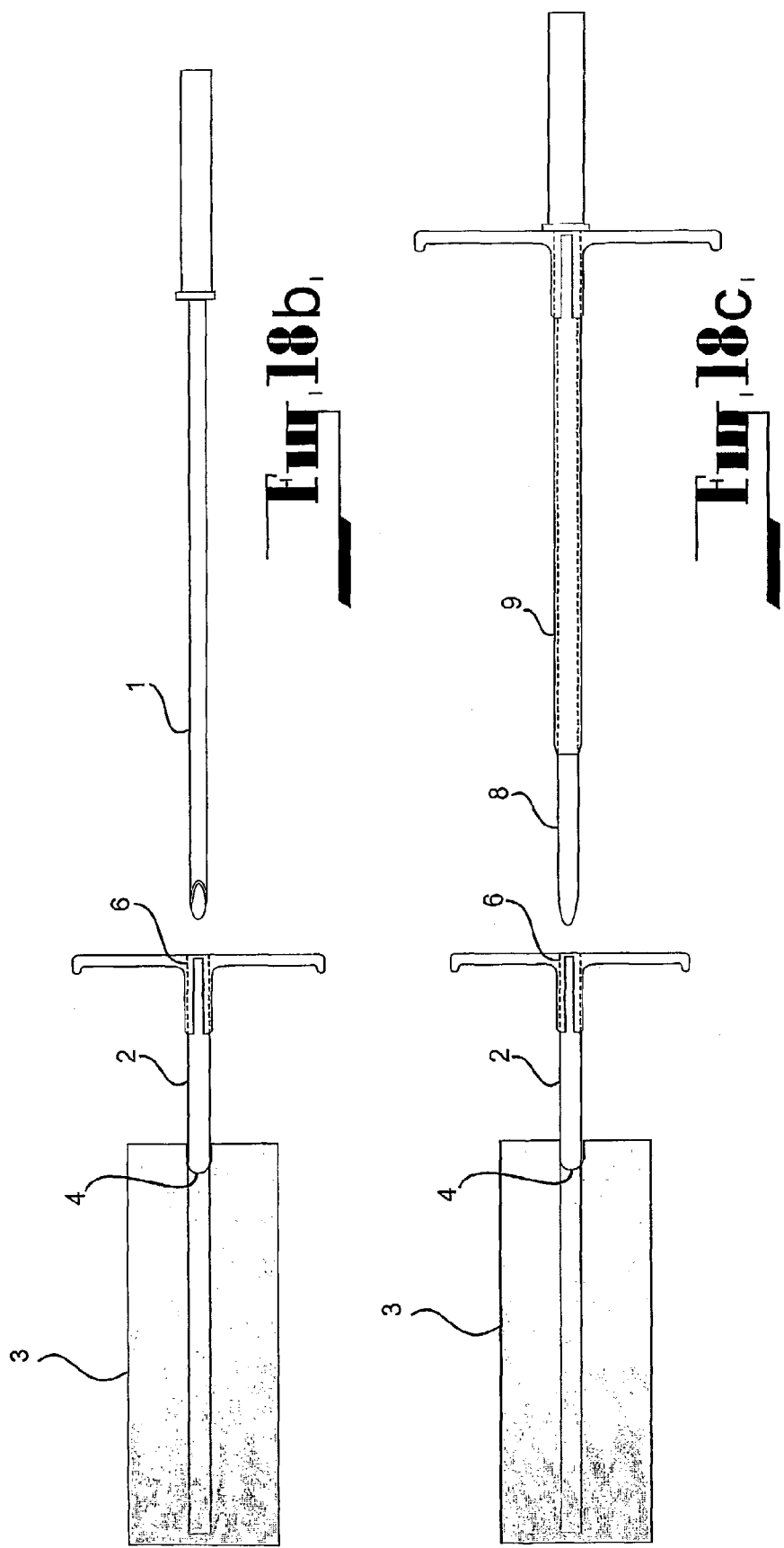

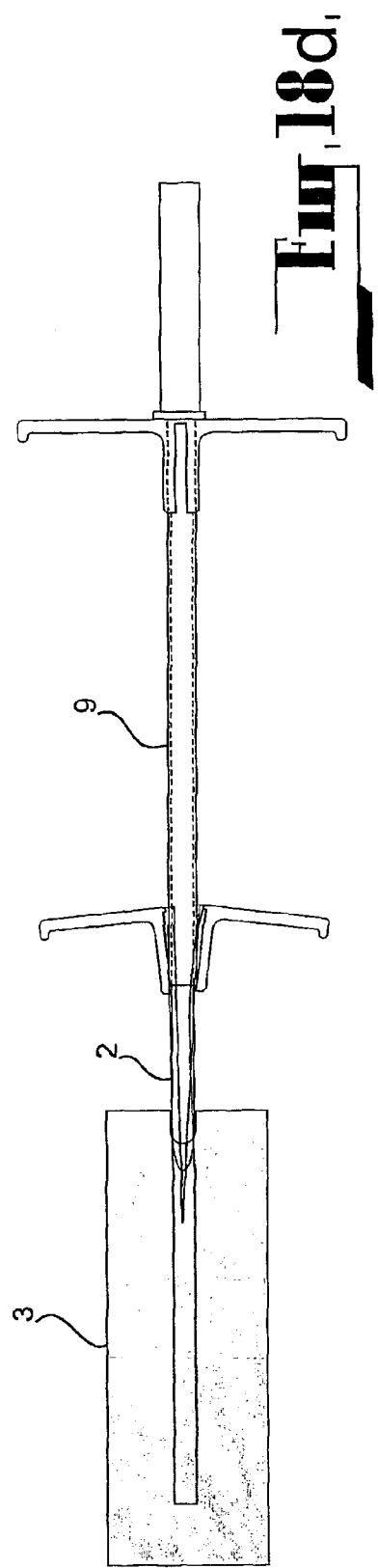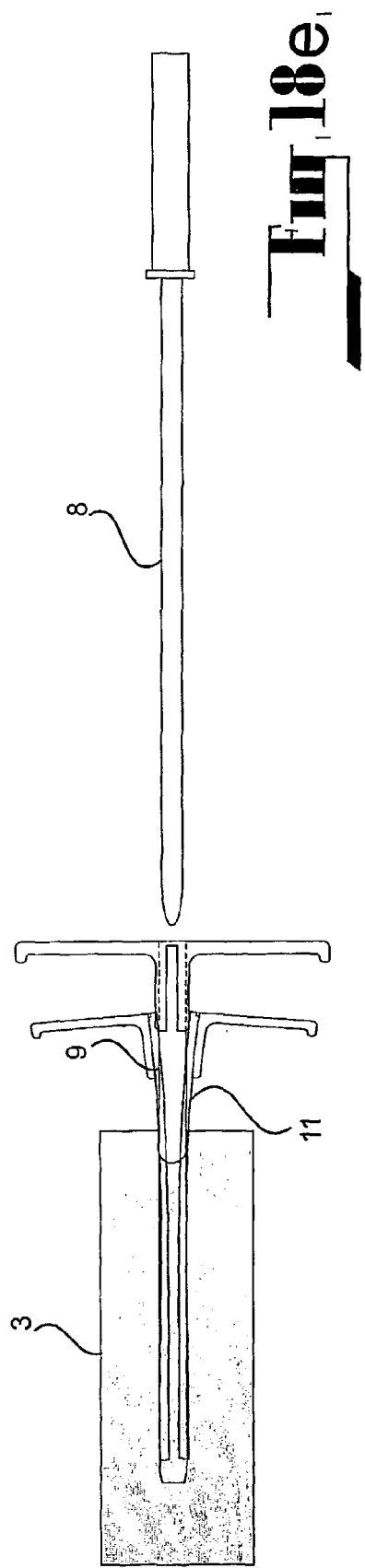

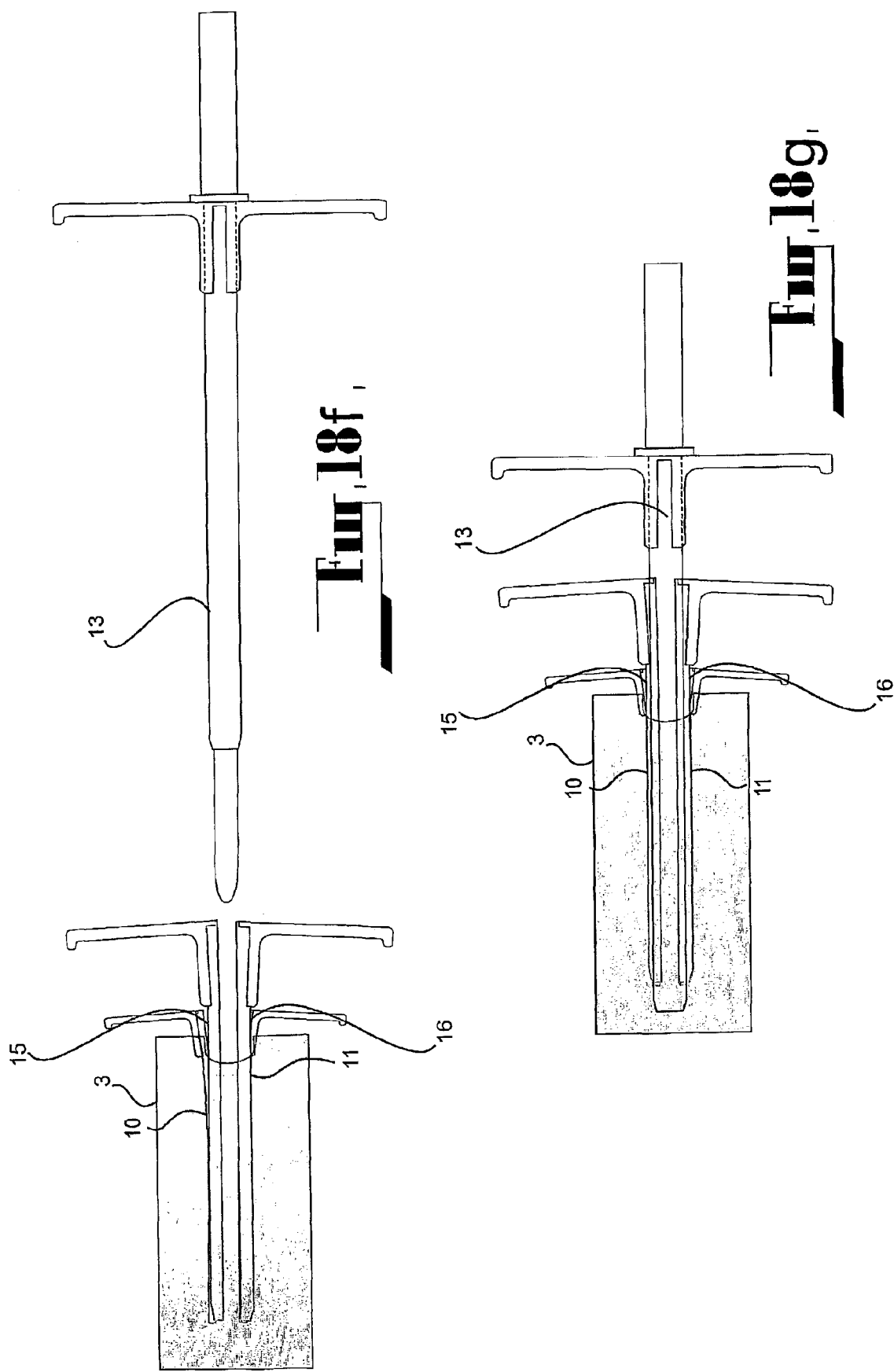

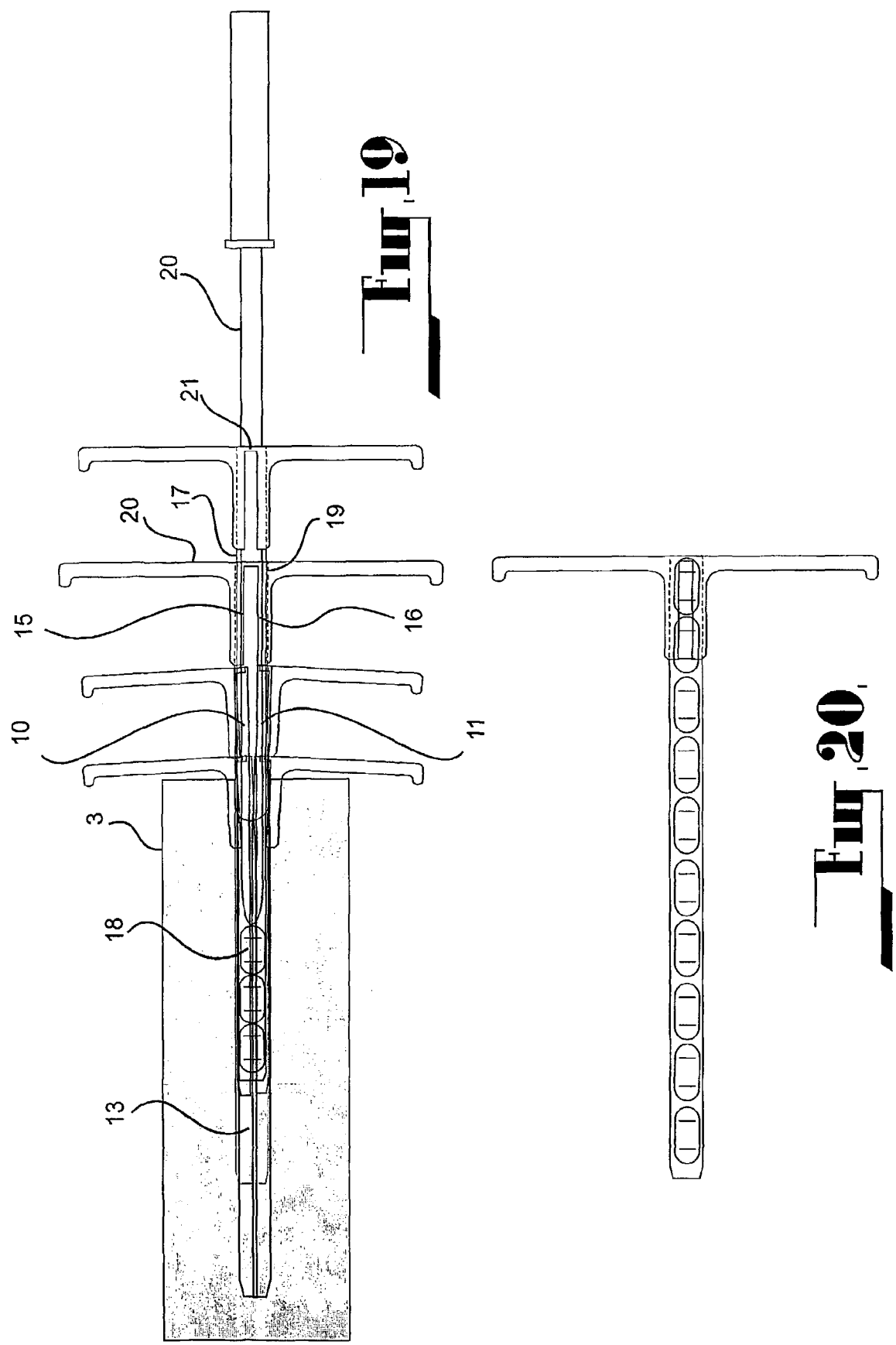

SLOW RELEASE PHARMACEUTICAL PREPARATION AND METHOD OF ADMINISTERING SAME

This application claims priority to PCT/AU01/011075 filed on Sep. 3, 2001, which claims priority to Australian Provisional application PQ 9851 filed on Sep. 1, 2000 and Australian Provisional application PQ 9852 filed on Sep. 1, 2000, the disclosures of which are hereby incorporated by reference.

FIELD OF THE INVENTION

The present invention relates to a pharmaceutical preparation capable of releasing an active agent or agents at a suitable therapeutic rate for a period of time without an initial burst release of active agent upon administration. In particular, the invention provides an improved implant for the sustained administration of a biologically active compound suitable for subcutaneous implantation. The invention also relates to methods for making, using and administering the preparation and the implant of the invention as well as a method of treating a patient using the preparation.

BACKGROUND ART

The benefits of sustained release pharmaceutical preparations are well known in the art. Many therapeutic agents have a short half-life and or are rapidly cleared (metabolised) from mammalian bodies requiring frequent or repeated administration of the therapeutic agent to bring about a therapeutic effect in a patient.

A wide variety of different sustained release pharmaceutical preparations are known in the art. Some sustained release pharmaceutical preparations are "matrix" type, and comprise an active compound dispersed in a matrix of a carrier material. The carrier material may be porous or non-porous, solid or semi-solid, and permeable or impermeable to the active compound. Matrix devices may be biodegradable, i.e., they may slowly erode after administration. Alternatively, matrix devices may be nondegradable, and rely on-diffusion of the active compound through the walls or pores of the matrix. Matrix devices may be easily prepared, but are not suitable for all compounds. Furthermore, it is difficult to prepare matrix devices that release active compound at a constant rate (i.e., zero order kinetics). Generally, the release rate is typically a function of the active compound's concentration in the matrix.

There are however, many problems with existing implants when used to administer therapeutic agents to patients. First, they deliver a high dose of active agent within a first few days of implantation before reaching a plateau rate of delivery for the majority of the lifespan of the implant. This is due to an initially high rate of absorption caused by the breakdown of the surface of the implant.

Second, irritation of tissues surrounding the implant site occurs because of the initial high rate of absorption of the active agent. This results in redness and soreness of the skin immediately around the implant.

Third, there is the problem that a constant rate of release of active agent over a long period of time is difficult to achieve. Generally, the release rate is typically a function of the concentration of the active agent.

A final problem is that existing implants have a relatively short lifespan.

Thus, there is a need for an improved implant, which deliver active agent at a therapeutic rate without an initial rise in concentration of the active agent for an extended period of time.

Throughout the specification, unless the context requires otherwise, the word "comprise" or variations such as "comprises" or "comprising", will be understood to imply the inclusion of a stated integer or group of integers but not the exclusion of any other integer or group of integers.

DISCLOSURE OF THE INVENTION

According to the present invention there is provided a pharmaceutical preparation adapted for sustained release of an active agent(s) over an extended period of time at a therapeutic rate without a significant burst release of the agent(s) upon administration, wherein the preparation comprises: (i) an outer portion prepared from one or more layers of a biodegradable polymer, which is selected to release an active agent over an extended period of time when positioned in situ in a patient, and (ii) an inner portion comprising a plurality of microcapsules formed from at least a biodegradable polymer, said microcapsules containing at least an active agent, wherein the microcapsules are compressed into the form of a tablet under suitable pressure to constrain the rate of release of the active agent from the microcapsules.

The rate at which an active agent is delivered to a patient may range depending on the therapeutic effect sought. According to the invention, pharmaceutical levels of an active agent in the patient rise to a desired therapeutic level where they will approximately remain over the life of the pharmaceutical preparation. To this extent, preparations of the present invention do not exhibit any significant burst effect of the drug when initially administered to the patient. A burst effect is commonly exemplified by a significant delivery rate rise in the pharmaceutical upon administration to the patient followed by a progressive decline in the delivery rate of the pharmaceutical.

The therapeutic level of the drug that is reached in the serum of the patient should be sufficient for treatment of a patient over an extended period of time and should not cause any ill effects to the patient. Preferably, the release rate is either relatively constant or declines slowly over the in situ life span of the tablet or it reduces as the preparation gradually degrades in situ. Most preferably, the release rate of the preparation decreases at a rate proportional to the length of time in which the preparation is in the patient. The preparation should, however, be prepared to ensure that the release rate of the active agent is such that an extended therapeutic effect is observed over the expected in situ life of the preparation in the patient.

In the process of preparing a pharmaceutical preparation in accordance with the invention particular attention must be had to the pressure used to prepare the inner tablet. The amount of pressure applied in the compression process is proportional to the lifespan of the implant and is inversely proportional to delivery rate. To produce a long lasting pharmaceutical preparation it is desirable to use a high pressure when forming a tablet from the active agent/polymer microcapsule mix. High pressures are used to weld the microcapsules together when forming the implant and thus increasing the strength of the tablet matrix and therefore increasing the durability of the implant. The compaction of the mixture into granulates may be by conventional dry compaction means, for example pressing, rolling, slugging extrusion etc. Preferably, a sufficiently high pressure should be used such that a force of at least 5 kg is required to fracture the surface of the implanted tablet. Still more preferable are pressures, which will require 6, 7, 8, 9, and 10 kg to fracture the surface of an implanted tablet. Another example of a preferable pressure is, the pressure reading of at least 50 on a Manesty tablet punching machine, model F3.

The size of the microcapsules used in the pellet also has an impact on the lifespan of the implant in a patient. The bigger the microcapsules the greater reduction in absorption of the active agent. Preferably, the size of the microcapsules is greater than 12 microns. In a preferred embodiment, where the active agent is naltrexone the size of a microcapsules is preferably between 30 to 100 microns.

The diameter of the pharmaceutical preparation can range from 3 mm to 12 mm Preferably, the diameter is 5 mm to 8 mm. More preferable is a diameter of 8 mm. The height of the pharmaceutical preparation can range from 3 mm to 15 mm. Preferably the height is 5 mm.

By encapsulating an active agent with one or more coatings of a biodegradable polymer to form microcapsules and by compressing those capsules into a tablet, the absorption rate of the active ingredient can be rapidly reduced, thus increasing the period of time that the active agent can act in the body. In particular, the inventors have found that a pharmaceutical preparation possessing the above characteristics has the effect of:
  a) removing the initial rise in concentration of active ingredient when the pharmaceutical composition is first implanted;
  b) producing a relatively constant delivery rate for the lifespan of the implant;
  c) eliminating irritation of the surrounding tissue area caused by the initial rise in concentration of the active ingredient when the pharmaceutical composition is first implanted; and
  d) increasing the duration of action of the implant.

To ensure clarity of the description that follows, the following definitions are provided.

The term "active agent" refers to a compound useful for effecting some beneficial change in the subject to which it is administered. For example, "active agents" within the scope of this definition include gastrointestinal therapeutic agents such as aluminium hydroxide, calcium carbonate, magnesium carbonate, sodium carbonate and the like; non-steroidal antifertility agents; parasympathomimetic agents; psychotherapeutic agents; major tranquilizers such as chlorpromazine HCl, clozapine, mesoridazine, metiapine, reserpine, thioridazine and the like; minor tranquilizers such as chlordiazepoxide, diazepam, meprobamate, temazepam and the like; rhinological decongestants; sedative-hypnotics such as codeine, phenobarbital, sodium pentobarbital, sodium secobarbital and the like; steroids such as testosterone and testosterone propionate; sulfonamides; sympathomimetic agents; vaccines; vitamins and nutrients such as the essential amino acids; essential fats and the like; antimalarials such as 4-aminoquinolines, 8-aminoquinolines, pyrimethamine and the like, anti-migraine agents such as mazindol, phentermine and the like; anti-Parkinson agents such as L-dopa; antispasmodics such as atropine, methscopolamine bromide and the like; antispasmodics and anticholinergic agents such as bile therapy, digestants, enzymes and the like; antitussives such as dextromethorphan, noscapine and the like; bronchodilators; cardiovascular agents such as anti-hypertensive compounds, Rauwolfia alkaloids, coronary vasodilators, nitroglycerin, organic nitrates, pentaerythritotetranitrate and the like; electrolyte replacements such as potassium chloride; ergotalkaloids such as ergotamine with and without caffeine, hydrogenated ergot alkaloids, dihydroergocristine methanesulfate, dihydroergocornine methanesulfonate, dihydroergokroyptine methanesulfate and combinations thereof; alkaloids such as atropine sulfite, Belladonna, hyoscine hydrobromide and the like; analgetics; narcotics such as codeine, dihydrocodienone, hydromorphine, meperidine, morphine and the like; narcotic antagonists such as naltrexone and naloxone and the like; non-narcotics such as salicylates, aspirin, acetaminophen, d-propoxyphene and the like; antibiotics such as the cephalosporins, chloranphenical, gentamicin, Kanamycin A, Kanamycin B, the penicillins, ampicillin, streptomycin A, antimycin A, chloropamtheniol, metromidazole, oxytetracycline penicillin G, the tetacyclines, and the like; anti-cancer agents; anti-convulsants such as mephenytoin, phenobarbital, trimethadione; anti-emetics such as thiethylperazine; antihistamines such as chlorophinazine, dimenhydrinate, diphenhydramine, perphenazine, tripelennamine and the like; anti-inflammatory agents such as hormonal agents, hydrocortisone, prednisolone, prednisone, non-hormonal agents, allopurinol, aspirin, indomethacin, phenylbutazone and the like; prostaglandins; cytotoxic drugs such as thiotepa, chlorambucil, cyclophosphamide, melphalan, nitrogen mustard, methotrexate and the like; antigens of such microorganisms as *Neisseria gonorrhea, Mycobacterium tuberculosis,* Herpes virus (humonis, types 1 and 2), *Candida albicans, Candida tropicalis, Trichomonas vaginalis, Haemophilus vaginalis,* Group B *Streptococcus ecoli, Microplasma hominis, Hemophilus ducreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis,* Equine herpes virus 1, Equine arteritis virus, IBR-IBP virus, BVD-MB virus, *Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani,* and the like; antibodies that counteract the above microorganisms; and enzymes such as ribonuclease, neuramidinase, trypsin, glycogen phosphorylase, sperm lactic dehydrogenase, sperm hyaluronidase, adenosinetriphosphatase, alkaline phosphatase, alkaline phosphatase esterase, amino peptidase, trypsin, chymotrypsin, amylase, muramidase, acrosomal proteinase, diesterase, glutamic acid dehydrogenase, succinic acid dehydrogenase, beta-glycophosphatase, lipase, ATP-ase alpha-peptate gamma-glutamylotranspeptidase, sterol-3-beta-ol-dehydrogenase, and DPN-di-aprorase. Other suitable active agents include testosterone, progesterone and estrogens such as diethyl stilbestrol, 17-beta-estradiol, estrone, ethinyl estradiol, mestranol, and the like; progestins such as norethindrone, norgestryl, ethynodiol diacetate, lynestrenol, medroxyprogesterone acetate, dimesthisterone, megestrol acetate, chlormadinone acetate, norgestimate, norethisterone, ethisterone, melengestrol, norethynodrel and the like; and spermicidal compounds such as nonylphenoxypolyoxyethylene glycol, benzethonium chloride, chlorindanol and the like. In one preferred embodiment, the active agent is naltrexone.

The term "effective amount" as applied to "one or more active agents" refers to that amount which is sufficient to effect the desired change in the subject. It is within the knowledge and skill of a person skilled in the art to determine the effective amount of an active agent.

By "microcapsules" is meant particles that contain an active agent dispersed or dissolved within a biodegradable, biocompatible polymer that serves as the matrix of the particle.

By "biodegradable" is meant a material that should degrade by bodily processes to products readily disposable by the body and should not accumulate in the body. The products of the biodegration should also be biocompatible with the body.

By "biocompatible" is meant not toxic to the human body, is pharmaceutically acceptable, is not carcinogenic, and does not significantly induce inflammation in body tissues.

The term "treatment" as used herein covers any treatment of a disease in an animal (including a human), and includes: (i) preventing the disease from occurring; (ii) inhibiting the disease, i.e., arresting its development; (iii) relieving the disease, i.e., causing regression of the disease; or (iv) modifying normal biological activity such as in the case of promotion of weight gain or contraception.

While the pharmaceutical preparations prepared herein may be administered in any form, preferably they are delivered as implants adapted for drug delivery beneath subcutaneous tissue.

The term 'implant(s)' refers to any object that may be required to be administered to a patient for a pharmaceutical effect including the pharmaceutical preparation of the present invention. For the purposes of this specification, the term 'implant(s)' refers to a pharmaceutical preparation comprising an active agent. In a preferred embodiment, the implant comprises at least naltrexone or like substance as the active agent.

The preparation of the invention can be administered to any mammal. Preferably, the mammal is a human being.

The effective amount of active agent can be determined by a person skilled in the art. When the active agent is naltrexone, the effective amount of naltrexone is about 1 g to about 20 g. Preferably, the effective amount is about 3 g to about 15 g. Still more preferable is a dosage range of about 3.6 g to about 7.2 g.

The implants of the present invention are adapted to deliver active agent at a constant rate for an extended period of time. Where the active agent is, for example, naltrexone the rate of delivery is preferably about 0.1 mg per day to 30 mg per day. More preferably the rate of delivery is 0.5 mg per day to 30 mg per day with delivery rates between 1 mg per day to 5 mg per day being even more desirable. Still more desirable are delivery rates between 3 mg per day to 10 mg per day. Most desirable are delivery rates of 3.6 mg per day to 14.4 mg per day.

Another way to express delivery rates is by multiplying the percentage of active agent delivered per day by the amount of active agent remaining in the implant. The percentage of active agent delivered per day can range from 1% per day to 10% per day. Preferably the percentage per day is 0.2% per day, 0.4% per day or 0.8% per day.

Preferably, the length of time which the implants can deliver active agent is for more than 40 days. More preferable is a duration of delivery of over 45 days. More preferable is a duration of delivery of over 50 days. More preferable is a duration of delivery of over 3 months. Still more preferably the duration of delivery is over 6 months. Even more preferably the duration of delivery is over 1 year. Still more desirable the duration of delivery is over 2 years. A preferred embodiment is a pharmaceutical composition comprising naltrexone having a lifespan of more than 40 days, more preferably more than 45 days, more preferably more than 50 days, more preferably more than 3 months, more preferably over 6 months and still more preferably over 1 year and even more desirably over 2 years. Still more desirable is a lifespan of at least 3 years.

One factor which contributes to the ability to achieve the duration periods described in the above paragraph is that the biodegradable polymer softens during a period which results in an increase in the release rate of active agent. The release rate is increased to a rate which is about the same as when the implant was first administered. Such an increase in release rate, increases the lifespan of the implant, provided that the rate of degradation of the biodegradable polymer is similar to the rate of release of active agent.

The polymeric matrix material of the microcapsules of the present invention is a biocompatible and biodegradable polymeric material. Preferably, the biodegradable polymer used in the preparation of the pharmaceutical preparation is long lasting. The matrix material should be biodegradable in the sense that the polymeric material should degrade by bodily processes to products readily disposable by the body and should not accumulate in the body. Preferably, the length of time that the biodegradable polymer stays intact is more than 40 days, more preferably the biodegradable polymer stays intact for a length of time of over 45 days. More preferably the biodegradable polymer stays intact for a length time of over 50 days. More preferably the biodegradable polymer stays intact for a length of time of over 3 months, still more preferably, more than 6 months and still more preferably more than 1 year. The coating should however allow the active agent to diffuse out of the implant and into the surrounding blood stream and its thickness can be altered to control this role. Therefore when the coating is present, the implant is still able to release active agent. Suitable examples of polymeric matrix materials include poly(glycolic acid), poly-D,L-lactic acid, poly-L-lactic acid, copolymers of the foregoing, poly (aliphatic carboxylic acids), copolyoxaates, polycaprolactone, polydioxonone, poly(ortho carbonates), poly(acetals), poly(lactic acid caprolactone), polyorthoesters, poly(glycolic acid-caprolactone), polyanhydrides, and natural polymers including albumin, casein, and waxes, such as, glycerol mono-and distearate, and the like. Purasorb-Poly DL-Lactide with an inherent viscosity in the range of 0.1 dl/g to 1.8 dl/g is preferable. The most preferred polymer for use in the practice of this invention is Purasorb-Poly DL-Lactide with a molecular weight of 24 800 and inherent viscosity of 0.50 dl/g. An example of another biodegradable polymer is Poly DL-Lactide/glycolide copolymer with inherent viscosity of 0.90 dl/g.

The inventors have also found that coating the compressed tablets formed from a plurality of microcapsules with one or more layers of a biodegradable polymer reduces the absorption rate of the active ingredient. Another effect of using a coating around the tablets is to reduce the risk of tissue irritation caused by direct contact of the active agent with surrounding tissue. Preferably, a tablet is coated with at least one layer of biodegradable polymer. It is more preferable if a tablet is coated with at least 2 layers of biodegradable polymer. It is even more preferable if a tablet is coated with at least 3 layers or more of biodegradable polymer.

A plurality of tablets can be coated with a biodegradable polymer to further reduce the absorption rate of the active agent. Thus two or more tablets can be formed into one pellet by coating the tablets with a biodegradable polymer. The rate of absorption of such a pellet is lower than that of an equivalent sized implant made from one tablet. This may be due to the number of coatings of biodegradable polymer and reduced surface area of active agent exposed. Preferably there is one coating of biodegradable polymer. More preferably, there are two coatings of biodegradable polymer. Still more preferably, there are three coatings of biodegradable polymer. Where a plurality of tablets are formed together as a single implant different tablets may have different release rates. For example, 0.4% and 0.2% tablets may be formed together in a single implant.

The pellets described above can contain one or more tablets comprising different active agents, each active agent having different rates of release. For example one tablet may comprise of oestrogen, a second tablet may comprise progesterone and a third tablet may comprise testosterone.

The thickness of the coating of biodegradable polymer surrounding the tablet may affect the absorption rate of the active ingredient. The greater the thickness of the coating, the greater the reduction in absorption rate of the active agent. Preferably the thickness of the coating is 0.001 mm to 1 mm. More preferably the thickness is 0.01 mm to 0.1 mm. Still more preferably the thickness is 0.1 mm to 1 mm. An example of a suitable thickness of the coating is 0.6 mm.

The microcapsule product used in the present invention can be prepared by any method capable of producing microcapsules in a size range acceptable for use in the compressed tablets. In these methods, the material to be encapsulated (ie the active agents) is generally dissolved, dispersed, or emulsified, using known mixing techniques, in a solvent containing the wall-forming material. Solvent is then removed from the microcapsules and thereafter the microcapsule product is obtained. An example of a conventional microencapsulation process is disclosed in U.S. Pat. No. 3,737,337 wherein a solution of a wall or shell forming polymeric material in a solvent is prepared. The solvent is only partially miscible in water. A solid or core material is dissolved or dispersed in the polymer-containing solution and, thereafter, the core-material-containing solution is dispersed in an aqueous liquid that is immiscible in the organic solvent in order to remove solvent from the microcapsules. Another example of a process in which solvent is removed from microcapsules containing a substance is disclosed in U.S. Pat. No. 3,523,906. In this process, a material to be encapsulated is emulsified in a solution of a polymeric material in a solvent that is immiscible in water and then the emulsion is emulsified in an aqueous solution containing a hydrophilic colloid. Solvent removal from the microcapsules is then accomplished by evaporation and the product is obtained.

The microcapsules can be mixed by size or by type so as to provide for the delivery of active agent to the patient in a multiphasic manner and/or in a manner that provides different agents to the patient at different times, or a mixture of agents at the same time.

Pharmaceutical excipient can also be used in the implants of the invention. Suitable excipient are well known in the art and include starch, cellulose, talc, glucose, lactose, sucrose, gelatin, malt, rice, flour, chalk, silica gel, magnesium stearate, sodium stearate, glycerol monostearate, sodium chloride and dried skim milk.

While pharmaceutical excipients may be incorporated in the inventive pharmaceutical preparation it should be observed that it is not desirable to incorporate significant amounts of disintegration agents that might have the effect of increasing the rate of degradation of the tablet. Such agents are preferably not included in the tablet formulation.

Pharmaceutical preparations prepared according to the invention will have broad application in treating patients in need of long term treatment of the active agents described herein. According to one embodiment the present invention provides a method of treating a patient by administering a pharmaceutical preparation as described herein to said patient.

According to one embodiment the invention provides a method of treating a patient comprising the steps of:
(1) administering implant(s) of the invention comprising about 3.6 g of naltrexone where 0.4% per day of the naltrexone mass is released;
(2) after about 3 to 6 months repeating step 1; and
(3) after about a further 6 months administering implant(s) of the present invention comprising about 3.6 g to 7.2 g of naltrexone where 0.2% per day of the naltrexone mass is released.

According to another embodiment the invention provides a method of treating a patient comprising the steps of:
(1) administering implant(s) of the present invention comprising about 1.8 g of naltrexone releasing at 0.2% per day and a second 1.8 g of naltrexone releasing at 0.4% per day;
(2) after about 90 days administering implant(s) of the present invention comprising about 3.6 g of naltrexone releasing at 0.2% per day; and
(3) if necessary, repeating step (2) after a period of 6 to 18 months.

According to a third embodiment there is provided a method of treating a patient who requires a greater rate of delivery per day than provided in the above embodiments. Such patients include those who are of large mass. This embodiment comprises the steps of:
(1) administering implant(s) of the present invention comprising about 1.8 g to 3.6 g where the percentage delivered per day is 0.4% and 0.2% respectively; and
(2) after about 12 months administering implant(s) of the present invention comprising 5.4 g naltrexone where 0.2% per day of the naltrexone mass is released.

It should be appreciated that the pharmaceutical preparation of this invention may be administered to a patient in any suitable manner for which the active agent(s) is designed to be administered. Most preferably, the preparation(s) are designed for subcutaneous administration, preferably in the subcutaneous tissue of the abdominal wall. In the alternative however, the preparations may be subcutaneously administered to other body cavities for example, vaginally, nasally and sublingually.

Accordingly one method for inserting one or more pharmaceutical preparations into a tissue of a mammal comprises the following steps:
a) making a single small incision into the tissue with a needle and first sheath;
b) withdrawing the needle from the first sheath, but leaving the first sheath in the tissue;
c) dilating the opening of the incision by inserting a dilator and second sheath of larger diameter through the bore of the first sheath;
d) withdrawing the dilator from the second sheath; and
e) dispensing the preparation by inserting it through the second sheath in the tissue.

If necessary, further dilation of the opening of the initial incision may be achieved by repeating the process of inserting dilators and sheaths of increasing diameter through the bore of sheaths of smaller diameter, until the diameter of the opening of the incision is sufficiently large to receive the preparation.

The abovementioned method will now be described in more detail, which should be understood as being preferably to the application of the method. Prior to making the incision with the needle an appropriate dose of local anaesthetic is administered to the site where the incision is to be made.

The diameter of the needle required for the initial incision is preferably less than 5 mm and desirably between 1 and 3 mm. In one example of the invention the diameter is 2 mm.

After the initial incision is made, the needle and sheath are inserted into the subcutaneous tissue of the patient. In this respect the needle desirably resides within the sheath and the two are inserted into the patient as a single unit. To aid penetration of the subcutaneous layer of the patient, the needle preferably protrudes from the sheath in such a manner that it may penetrate the epidermis of a patient before the sheath penetrates the epidermis. In an alternate form, the needle and sheath may be formed as a single unit wherein the needle or central body may be withdrawn from the sheath when inserted into a patient. Where the needle and sheath are formed as a single unit, preferably the sheath is adapted to penetrate a patient's tissue.

Following insertion and location of the needle and sheath, the needle is withdrawn from the sheath leaving the sheath in position protruding into the subcutaneous tissue. In order to dilate the opening of the incision, a dilator and sheath of larger diameter are inserted through the bore of the sheath in the subcutaneous tissue, thereby splitting the sheath left inside the subcutaneous tissue. The split sheath and the sheath and dilator of larger diameter remain in the subcutaneous tissue.

Further dilation of the opening of the incision may be required, depending on the size of the implant(s), which are to be administered. The opening of the incision is further dilated by inserting dilators and sheaths of increasing diameter into the bore of a sheath of smaller diameter, which remains in the subcutaneous tissue.

Dilation is required until such time as the opening of the incision is of a sufficient size to receive the implant(s).

Once the opening of the incision is of a sufficient size to receive the implant(s), the last dilator is withdrawn, but the accompanying sheath is left in the subcutaneous tissue site. A sheath of smaller diameter containing the implant(s) is pushed through the bore of the sheath, which has been left in the subcutaneous tissue. The dilator accompanying the sheath containing the implant(s) is then used to push the implant(s) through the sheath into the subcutaneous tissue.

According to the above method a plurality of implant(s) associated with each dose of active agent are capable of being delivered to a range of areas in the subcutaneous tissue of a patient along one incision track. While any number of implants may be delivered by this means, preferably at least 1 to 20 and more preferably 2 to 15 implants are delivered in a single track. Where multiple implants are delivered the implants are preferably spaced apart. For example, with the one incision, a 1 gram pellet can be spread into the areas at or near the incision, another gram may be delivered further up along the incision track and so on until the requisite number of grams of drug are delivered. Because the subcutaneous fat behaves like fluid, the implant(s) are not restricted to staying along the incision track. The implant(s) can be manipulated from the surface by a finger to spread them around. This reduces the discomfort to the patient of a single large implant. Furthermore, a large dose of drug can be administered from the one incision.

The method for insertion described above has the potential to alleviate the problems associated with delivery of medium and large implant(s). Using this methodology it is possible to deliver one or more implant per incision, thus being able to deliver a large dose of active agent in smaller sized pellets, the patient thus not feeling the discomfort of being inserted with one large pellet. Where more than one implant is delivered to the patient according to the above method, preferably the implants are inserted into the second sheath and forced through it with the aid of the dilator or a like device facilitating extrusion of the implant from the sheath. Where multiple implants are delivered to a patient the sheath may be withdrawn from the initial incision as the implants are released or all the implants may be extruded from the sheath before it is extracted.

BRIEF DESCRIPTION OF THE DRAWINGS

FIGS. 18 and 18a shows the insertion of a needle and sheath into subcutaneous tissue.

FIG. 18b shows the withdrawal of the needle from the sheath.

FIGS. 18c to 18h show dilation of the opening of the incision with a number of dilators and sheaths.

FIG. 19 shows the delivery of a plurality of implant(s) by insertion of at least dilator into a sheath containing one or more implant FIG. 20 shows a sheath containing implant(s).

BEST MODE(S) FOR CARRYING OUT THE INVENTION

Further features of the present invention are more fully described in the following Examples. It is to be understood that the present invention is not to be limited in scope by the specific embodiments described herein, which are intended for the purpose of exemplification only. Functionally equivalent products, compositions and methods are clearly within the scope of the invention as described herein.

EXAMPLE 1

Implantable Naltrexone

Figure 1:
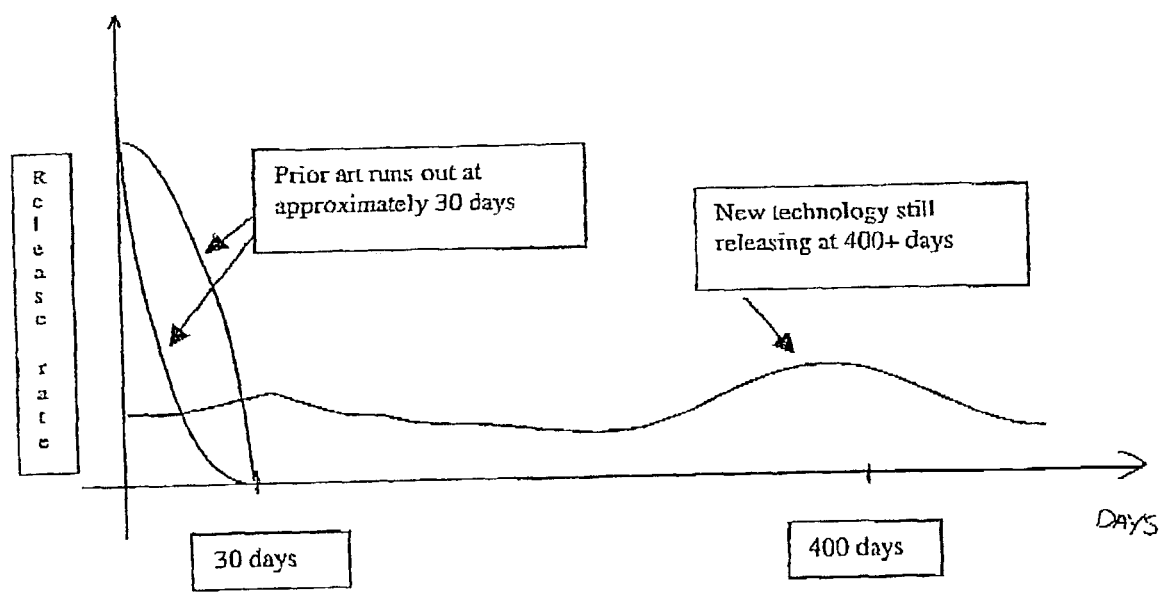
FIG. 1 is a graph showing release rate of prior art implants compared to the release rate of implants of the present invention.

Previously, patients have put up with an initial bolus dose when an implant is first inserted—commonly known as the "Burst Effect" (see FIG. 1).

Clinical work shows that for a Naltrexone implant to be effective, the implant should deliver an equivalent dose of 6-800 μg of Naloxone/hour. As Naltrexone is thought to be twice as effective as Naloxone as well as lasting 8 times as long in the body (ie $t_{1/2}$ Naloxone=½ hour, $t_{1/2}$ Naltrexone=4 hours), a dose greater than 40 μg/hr of Naltrexone might be potentially effective, as 40 μg/hr is close to being 1 mg/day. Therefore a 1 g Naltrexone implant releasing 0.1% per day should partially block receptors for a period of 1-2 years. Further, 7.2 g of naltrexone releasing at 0.2% per day should block receptors for 2 years.

The present invention allows naltrexone to be delivered in a reliable fashion for periods greater than 6 weeks. The herein described pharmaceutical preparation achieves a delivery of 0.5 to 10 mg/day and a corresponding blood level of 0.5 to 3 ng/ml and this is expected to be sufficient to block 15 to 300 mg of Morphine delivered intravenously. Furthermore, preparations prepared according to the invention can maintain sufficient blood levels for at least 3 months, preferably at least 3 years.

To achieve a reliable release rate for 3 months, a 1 g implant would need to release 2 to 10 mg of drug per day (ie 100 day lifespan≅3 months). A reliable release rate of 6 months may be achieved by a 3.6 g implant releasing at 14.4 mg/day, 2 g implant releasing 10 mg/day or a 1 g implant releasing 2 to 5 mg per day. For a period of 12 months, a 2 g implant releasing at 1 to 6 mg/day will have a lifespan of 300 to 1000 days ie approximately equal to 1 to 3 yrs or two 3.6 g implants releasing at 14.4.mg/day administered at 0 and 6 months. A period of 18 months may be achieved with a 2 to 3 g implant releasing at 1 to 10 mg/day or two 3.6 g implants administered at 0 and 6 months releasing at 14.4 mg/day and one 7.2 g implant administered at 12 months. A 3 g implant releasing at 0.5 to 10 mg per day may last for 2 years or longer. Two 3.6 g implants administered at 0 and 6 months releasing at 14.4.mg/day and one 7.2 g implant administered at 12 months releasing at 14.4 mg/day may last for 2 years or longer.

Figure 2:
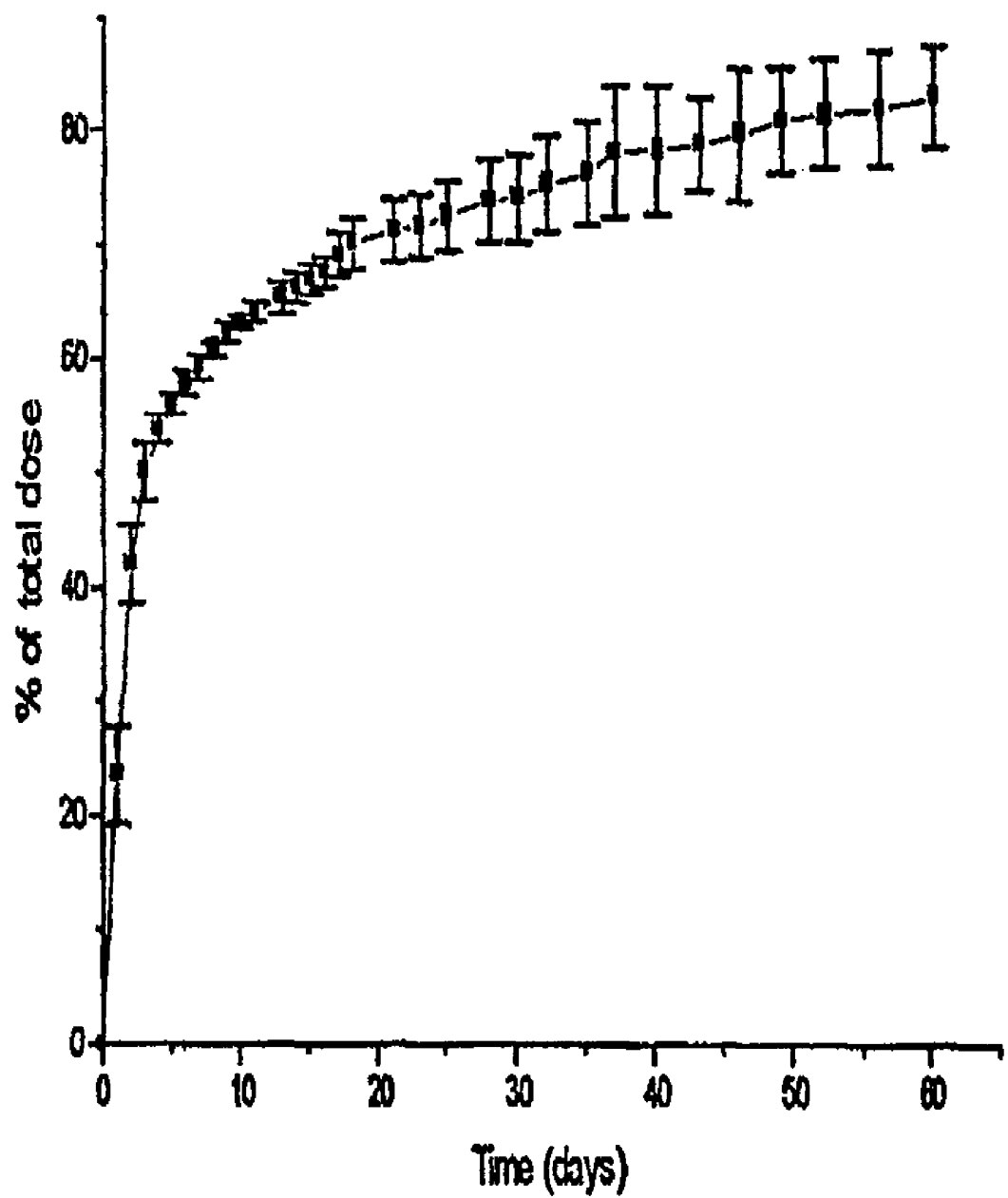
FIG. 2 is a graph showing the release rate of encapsulated microcapsules of naltrexone with Poly-DL-lactide in vitro.
Figure 3:
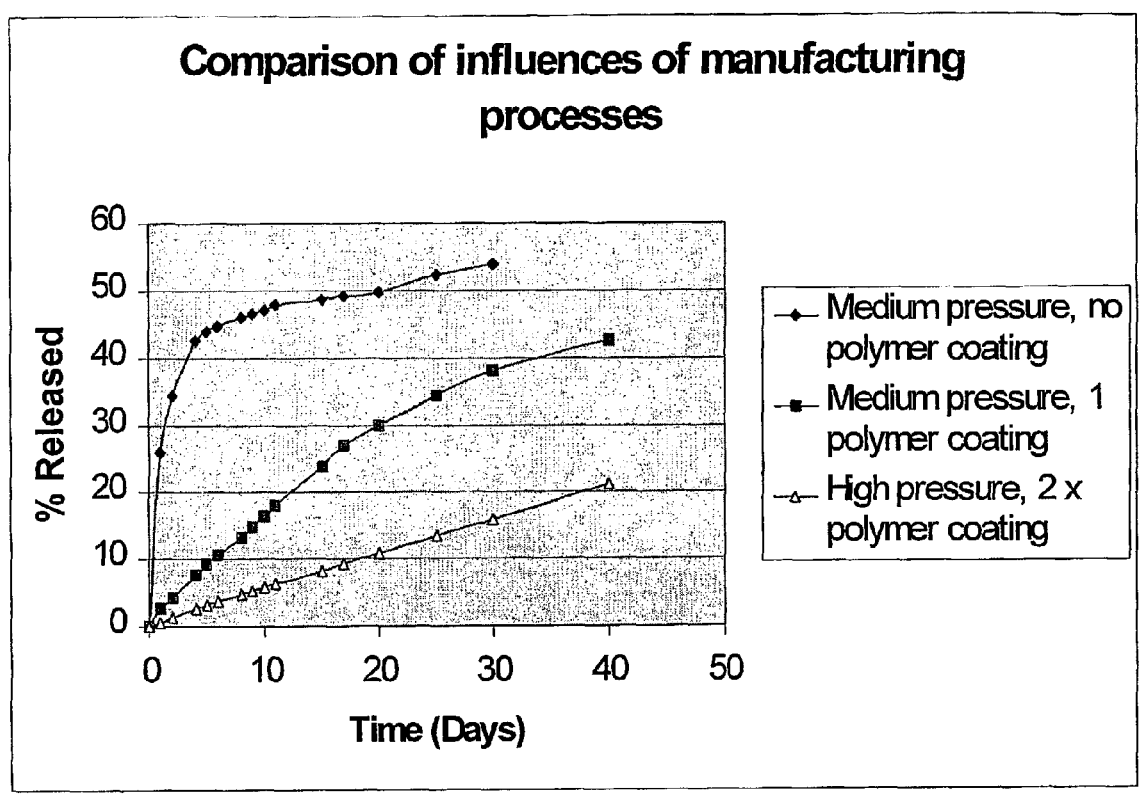
FIG. 3 is a graph showing the effects of pressure and polymer coating on the release rates.

Experimental results has identified the following as being pertinent to achieve said release rates:

1. Encapsulating Naltrexone with a long lasting polymer (Poly-DL-lactide), to form microcapsules of Naltrexone and polymer produced a release rate profile with an initial peak before stabilising and releasing at a relatively constant rate for greater than 2 months (see FIG. 2). The ratio of naltrexone to Poly-DL-lactide used was 1:1.
2. Punching a tablet from the encapsulated microcapsules under moderate pressure and coating the entire implant with Poly-DL-lactide eliminated the initial peak in the release rate as well as increasing the lifespan of the implant (see FIG. 3).
3. Coating the tablet a second time (ie increasing the thickness of the Purasorb Poly-DL-lactide coating)—estimated thickness of 0.5 mm and increasing the pressure used to punch the tablet helped to keep a linear release rate profile as well as further increasing the lifespan of the implant—see FIG. 3
4. Experiments were conducted on the effects of the surface area of the implant with respect to the volume of the tablet. It was shown that by reducing the ratio of the surface area to the volume of the tablet, an increase in the lifespan was measured. This is confirmed by experiments which demonstrate that a 5 mm diameter implant released Naltrexone at a rate of 0.6% per day in comparison to an 8 mm diameter tablet which released Naltrexone at 0.25% per day.
5. Another method of forming the implant was implemented to further increase the lifespan of an implant. Punching 5 tablets of 5 mm diameter and 1 mm high from encapsulated microcapsules of naltrexone and individually coating these implants (ie creating a series of "pancakes"), with Purasor Poly DL and then holding these 1 mm high tablets together and further coating the lot with Poly-DL-lactide to form one implant, the lifespan of the implant was much greater than an equivalent sized implant made from one pellet. This may be due to the coatings and reduced surface area which delayed absorption by 4 times—see Table 1 and FIG. 3.

TABLE 1

Influence of various manufacturing processes on the release rate of naltrexone (ACTUAL VALUES):

| Days | % Released, medium pressure, no polymer coat | % Released, medium pressure, 1 polymer coat | % Released, high pressure, 2 polymer coats |
|---|---|---|---|
| 0 | 0 | 0 | 0 |
| 1 | 26.01 | 2.69 | 0.64 |
| 2 | 34.36 | 4.22 | 1.43 |
| 4 | 42.52 | 7.73 | *2.54 |
| 5 | 43.92 | *9.13 | 3.1 |
| 6 | 44.75 | *10.53 | 3.7 |
| 8 | 45.98 | 13.33 | *4.73 |
| 9 | *46.55 | 14.83 | *5.24 |
| 10 | 47.12 | *16.34 | *5.75 |
| 11 | 47.79 | *17.86 | *6.27 |
| 15 | *48.68 | *23.92 | 8.32 |
| 17 | *49.13 | 26.95 | *9.33 |
| 20 | 49.8 | *29.76 | *10.84 |
| 25 | 52.32 | 34.43 | *13.36 |
| 30 | 53.79 | 38.05 | 15.9 |
| 40 | — | 42.61 | 21.23 |

*- Interpolated values

7. In order to eliminate the organic solvent from the tablet that was used in the coating of the tablet, the coated implant was stored under pressure that was slightly lower than atmosphere pressure and in a hot room overnight to evaporate the solvent from the tablet. The solvent evaporating point was 39° C. and the hot room was maintained at 50° C. thus such conditions would allow any solvent remaining in the tablet to evaporate overnight.

8. Using a single long implant has the disadvantage of causing the patient discomfort pain or possibly breaking the implant if the patient were to bend or move tissue around the implant site. Thus the method of using a series of pellets to achieve the required mass of the implant was developed so that any movement of the surrounding tissue site could be accommodated by the implant without causing any patient discomfort or breakage of the implant. This also allows injections of cassettes of spheres or tablets into an area of subcutaneous tissue.

The use of the described technique on implants was verified by laboratory water bath experiments and human blood serum level experiments. The laboratory water bath experiments demonstrated that implants made from the above techniques were releasing 0.2% per day and 0.4% per day in buffer solution. This predicts a lifespan in the order of 1-2 years. The human blood serum level experiments demonstrated that implants made from the above techniques were releasing 0.2%, 0.4% and 0.8% per day. This predicts a lifespan of the order of 1 to 2 years.

EXAMPLE 2

The following example demonstrates how the invention can be used to develop a custom implant, which can release individual drugs at varying rates according to the design.

Hormone replacement therapy can currently be delivered by means of slow release transdermal patches, oral tablets or implants. Typical hormones used are oestrogen, progesterone and testosterone. The prior art consists of individual implants of said hormones, which typically last for periods of 1 to 4 months.

Transdermal patches such as Estraderm, typically have to be replaced every 4 days. This lifespan is relatively short when compared to the required treatment time. Another problem associated with transdermal patches are problems encountered by varying absorption rates through different types of skin.

Quite often a combination of hormones can be used as opposed to individual hormones. In some instances, a combination of hormones may prove to be a more effective means of hormone replacement therapy.

Orally administered hormone tablets are another version of the prior art. Problems arise from the failure to maintain oral tablets. Reasons for the failure may be attributed to the inconvenience of having to take the tablets daily, forgetting to take the tablets daily or ceasing treatment due to the emotional stigma of having to remain on hormone replacement tablets.

Figure 4:
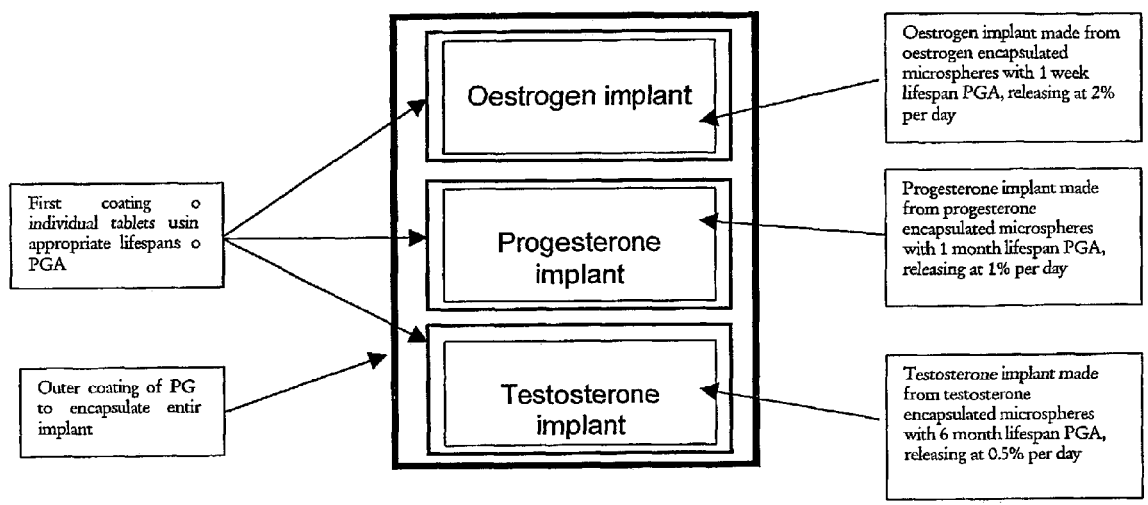
FIG. 4 is a custom design implant to release specific drugs at appropriate rates.

Through methods discussed in this invention, a custom implant may be designed to deliver a combination of the above hormones at rates appropriate to each hormone. Such a varied delivery system may be built into the one implant as illustrated in FIG. 4.

In order to achieve a variety of release rates from the one implant, the following procedure may be used.

To achieve a release rate of:

2% per day of oestrogen  
1% per day progesterone  } All from the one implant  
0.5% per day testosterone Thus according to this example oestrogen was encapsulated in microcapsules prepared from 1 week lifespan PGA polymer. The oestrogen tablets were then punched under maximum pressure. These tablets were then coated with 1 month lifespan PGA polymer.

Further progesterone was encapsulated in microcapsules prepared with 1 month lifespan PGA polymer. The progesterone tablets were then punched under maximum pressure and were coated with 1 month lifespan PGA polymer.

Finally testosterone was encapsulated in microcapsules prepared from 6 month lifespan PGA polymer. Testosterone tablet were then prepared under maximum pressure and coated with 6 month lifespan PGA polymer All three hormone implants were then stacked together coated with 6 month lifespan PGA polymer. With this formulation, an implant may be generated according to FIG. 4, with each individual drug releasing at an appropriate rate specific to that drug.

EXAMPLE 3

Naltrexone Delivery Rates in Rats

Figure 5:
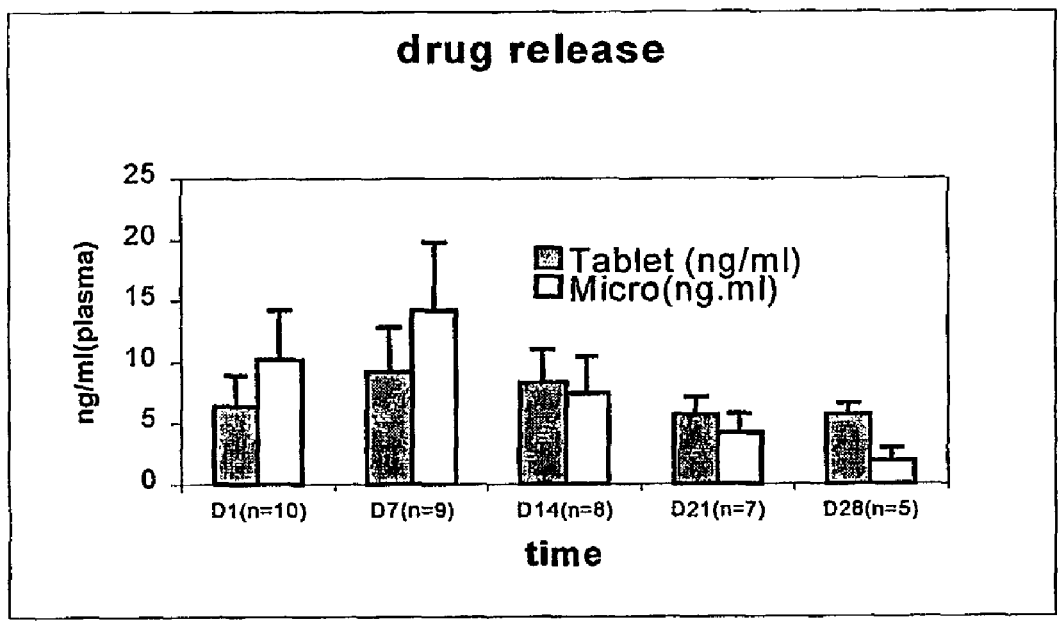
FIG. 5 is a graph showing naltrexone levels in the blood plasma of rats. The results obtained suggested the amount of drug released in vivo on a daily basis. After implantation of the tablets and microcapsules, plasma naltrexone level increased to a peak of 9.2 ng/ml and 14.2 ng/ml, respectively. Possibly, there was an initial burst release of naltrexone from the microcapsules between day 1 and 7. The relatively constant plasma level of naltrexone suggested a relative constant release rate of naltrexone from the tablets. In contrast, the naltrexone microcapsules showed rapid drug release in two weeks after administration. This difference in drug release rates may be due to the larger surface area per unit volume, and the smaller diameter.

To measure naltrexone plasma levels rats were implanted with naltrexone implants produced according to the present invention. FIG. 5 presents data showing naltrexone levels in the blood plasma of rats. The results obtained suggested the amount of drug released in vivo on a daily basis. After implantation of the tablets and microcapsules, plasma naltrexone level increased to a peak of 9.2 ng/ml and 14.2 ng/ml, respectively. Possibly, there was an initial burst release of naltrexone from the microcapsules between day 1 and 7. The relatively constant plasma level of naltrexone suggested a relative constant release rate of naltrexone from the tablets. In contrast, the naltrexone microcapsules showed rapid drug release in two weeks after administration. This difference in drug release rates may be due to the larger surface area per unit volume, and the smaller diameter.

EXAMPLE 4

Water Bath Experiments With Naltrexone Delivery Rates

The following water bath research was carried to establish that naltrexone tablets have release rates for the 0.2%/day implants.

Figure 6:
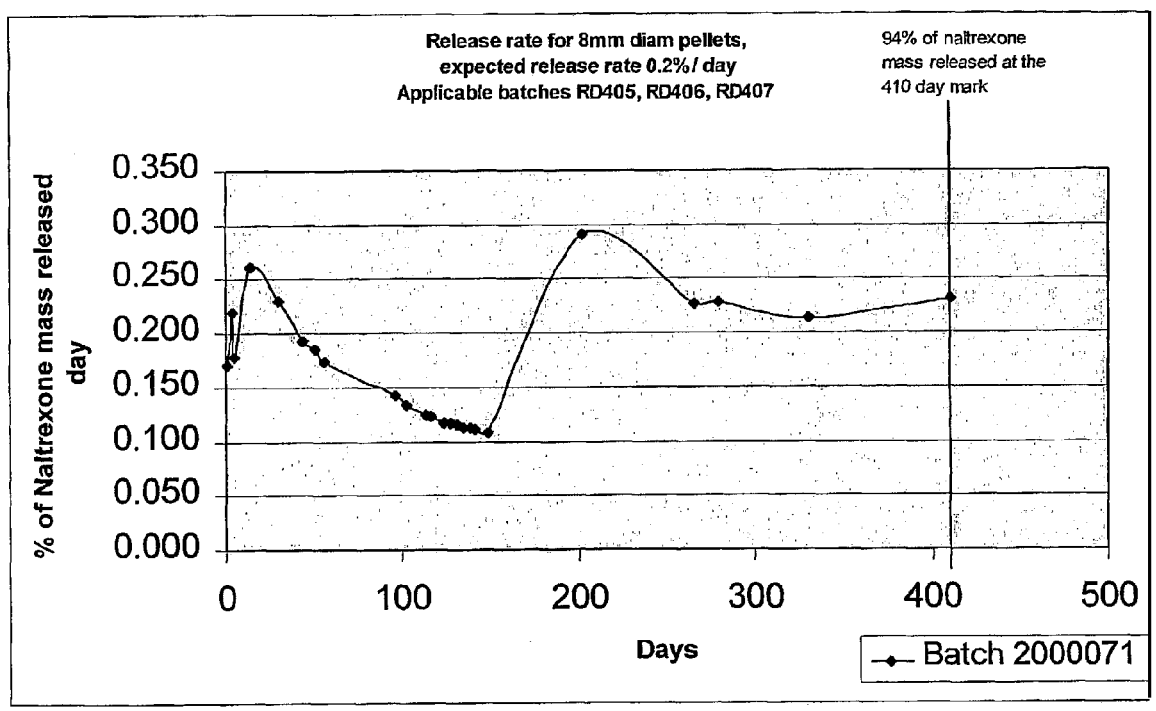
FIG. 6 shows release rates of naltrexone implants in a water bath expected to release 0.2% naltrexone per day. This graph shows 94% of naltrexone was released at about day 410 and the overall daily release is fairly consistent.
Figure 7:
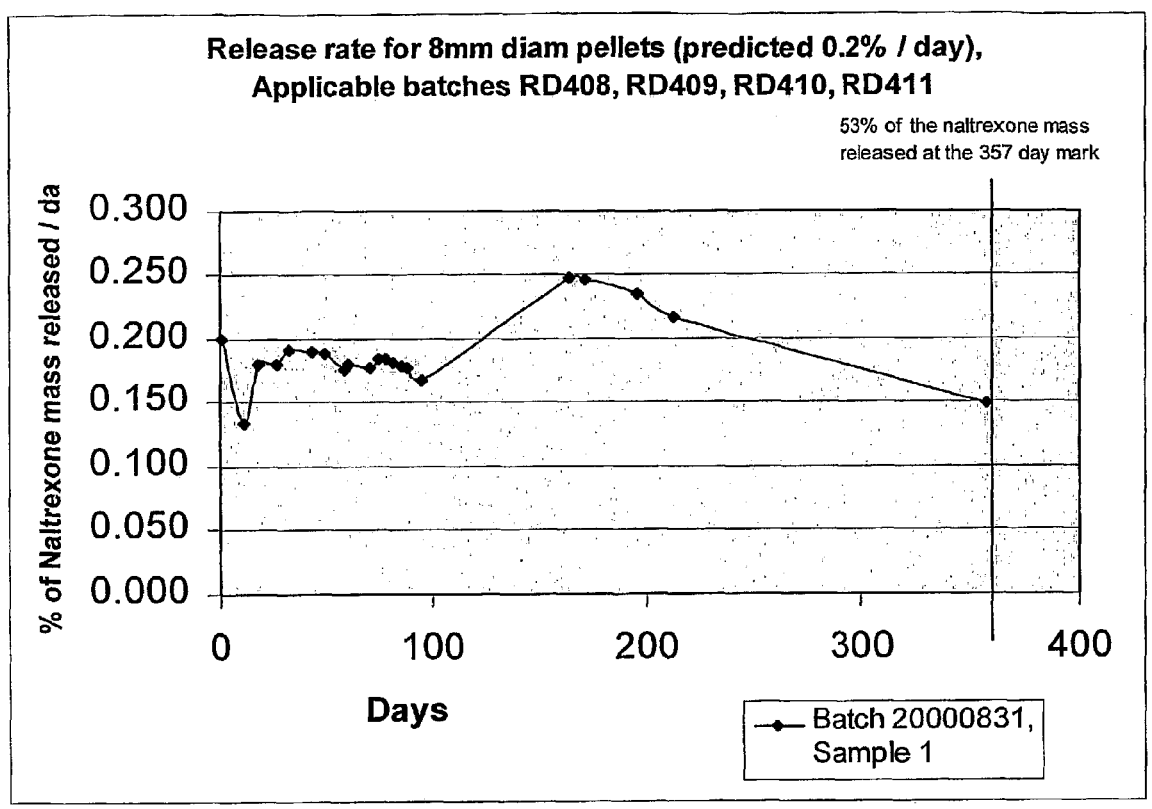
FIG. 7 shows release rates of naltrexone implants in a water bath expected to release 0.2% naltrexone per day. This graph shows 53% of the naltrexone was released at the 357 day mark and the overall release rate is fairly consistent.
Figure 8:
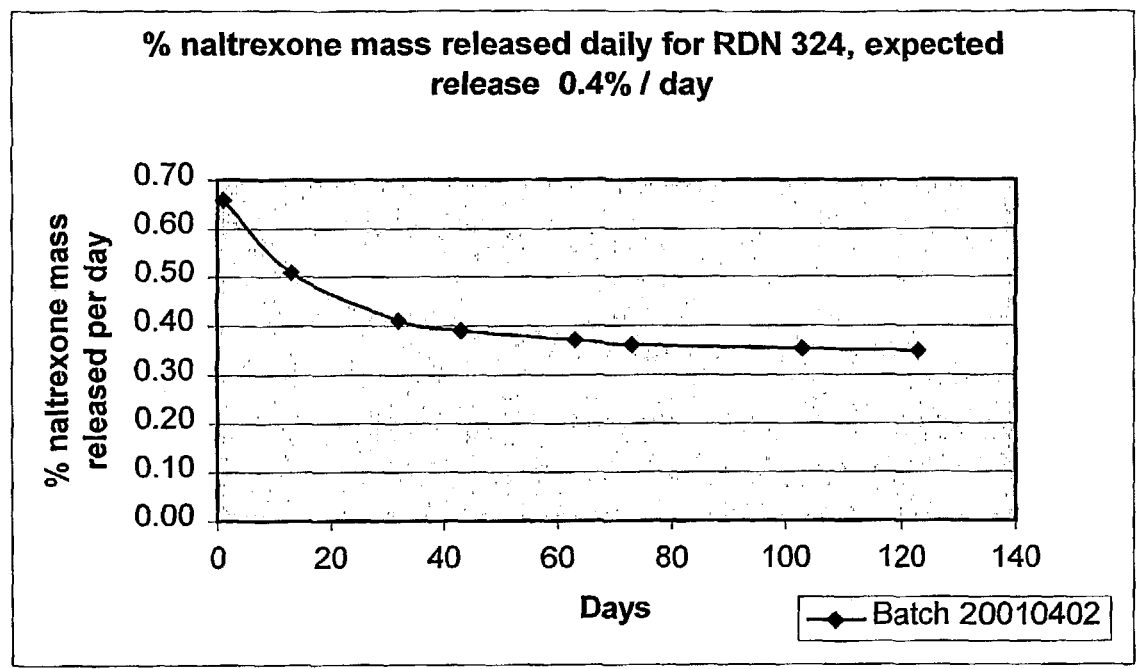
FIGS. 8 to 12 shows release rates of naltrexone implants in a water bath expected to release 0.4% naltrexone per day. The graphs show that the release rate is consistent for at least the first 120 days and at about 120 days the implants have released about 35-40% of the naltrexone.
Figure 9:
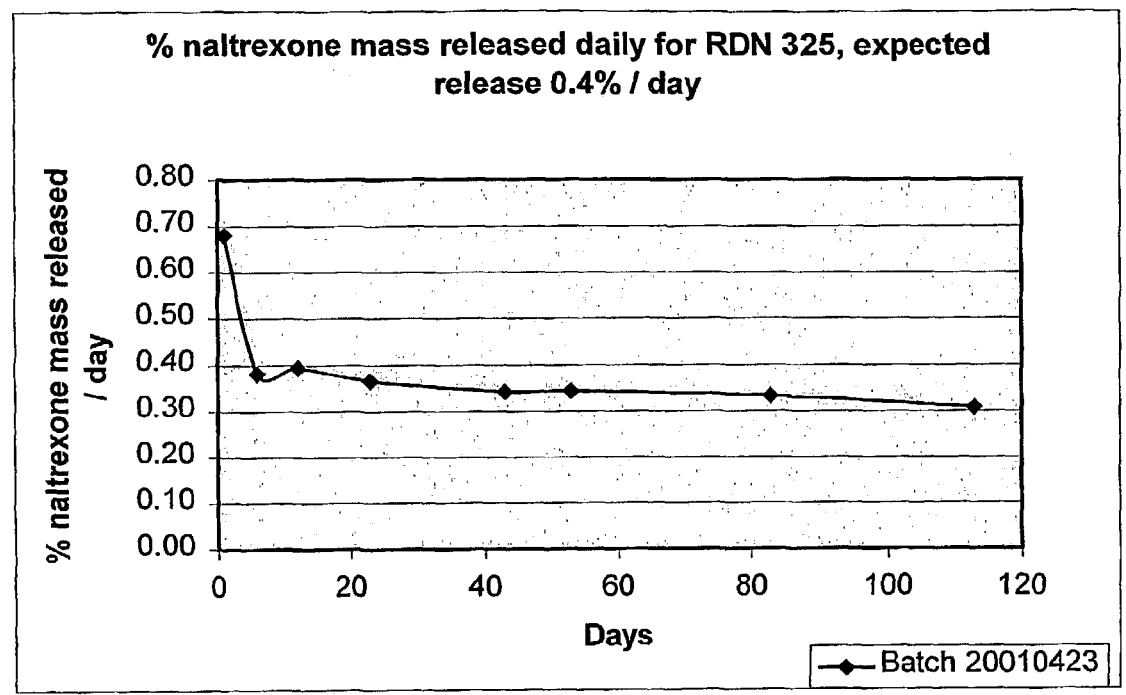
Figure 10:
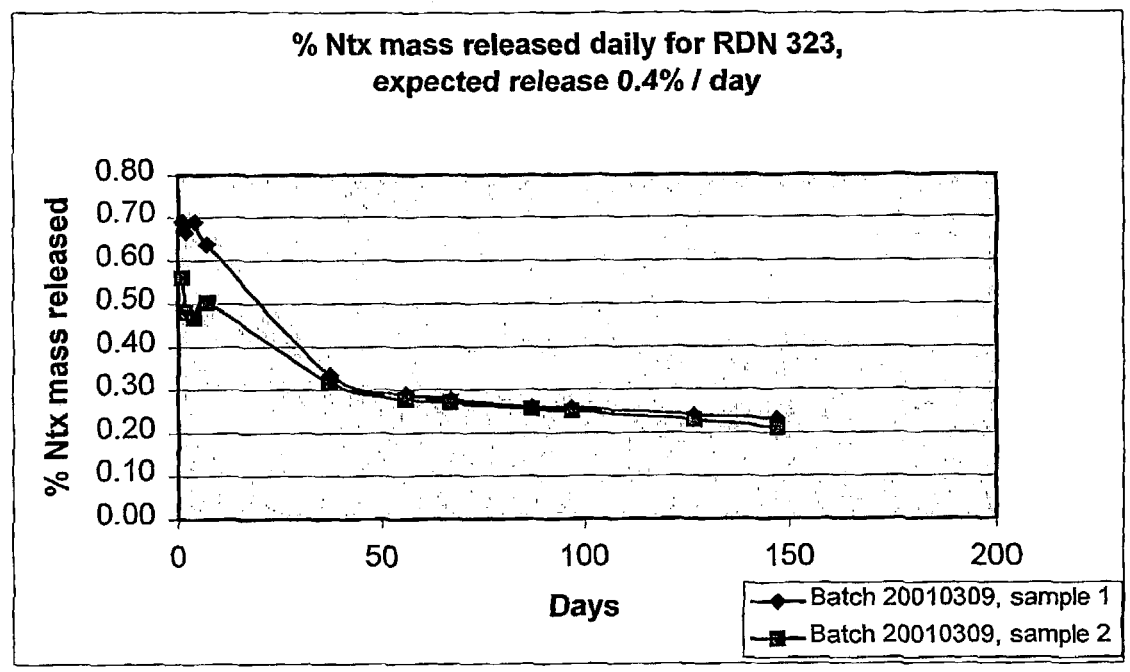
Figure 11:
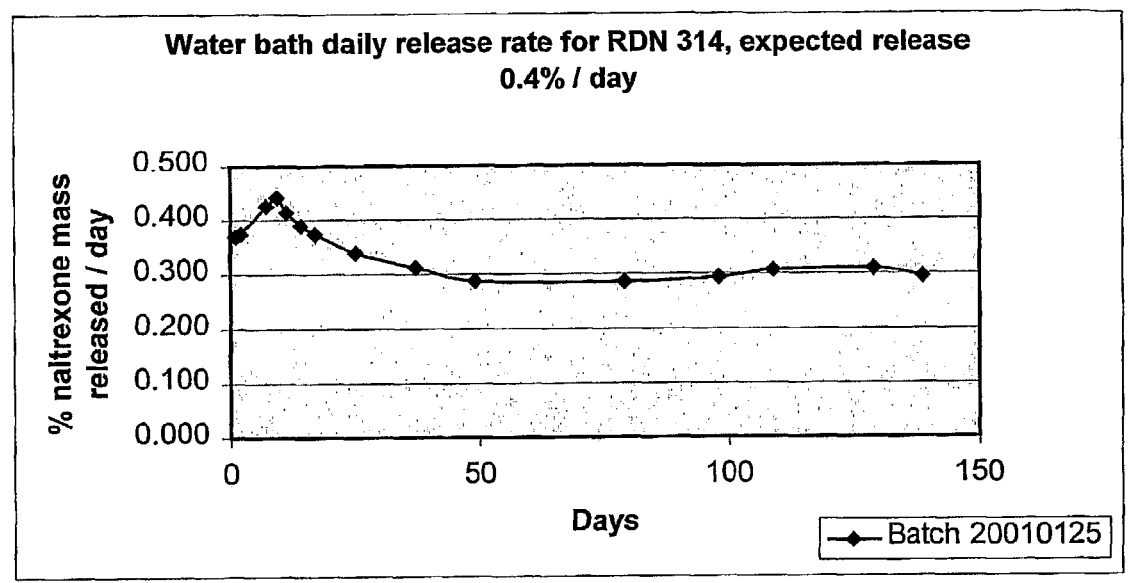
Figure 12:
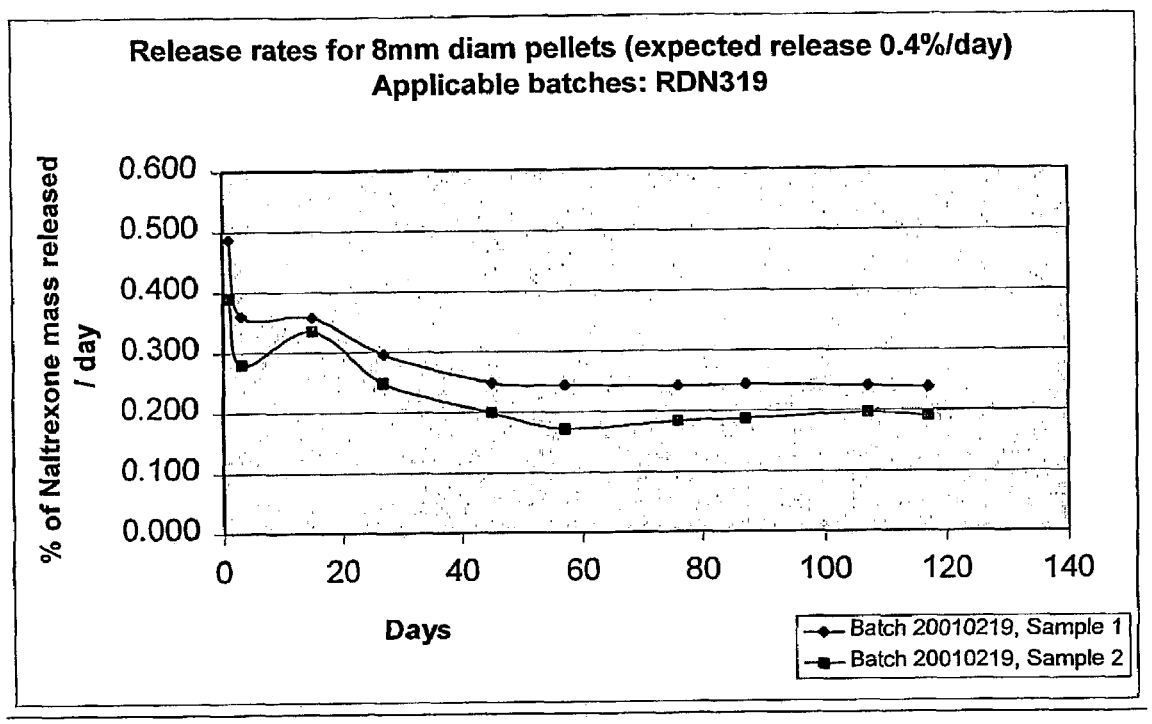

8 mm Tablets comprising naltrexone as the active ingredients produced according to the present invention were subjected to water bath examination Data from these experiments are presented in FIGS. 6 and 7. FIG. 6 shows 94% of the naltrexone mass released at day 410 and the overall daily release rate is pretty consistent. FIG. 7 shows 53% of the naltrexone mass released at the 357 day mark, the overall release rate is also pretty consistent. Note that during a corresponding period in FIG. 6, the total release was around 70%. This difference illustrates differences between manual punching which was used to produce the tablets used in FIG. 6 and automatic punching which was used in FIG. 7—the pressure of the punch in FIG. 7 is higher and is what we are currently using.

Therefore based on the data in FIG. 7 a 0.2%/day implant should continue to release active ingredient till the 500+day mark. Data in FIG. 6 shows release of active agent to the 410 day mark.

FIGS. 8 to 12 shows release rates of naltrexone implants in a water bath expected to release 0.4% naltrexone per day. The graphs show that the release rate is consistent for at least the first 120 days and at about 120 days the implants have released about 35-40% of the naltrexone.

Figure 13:
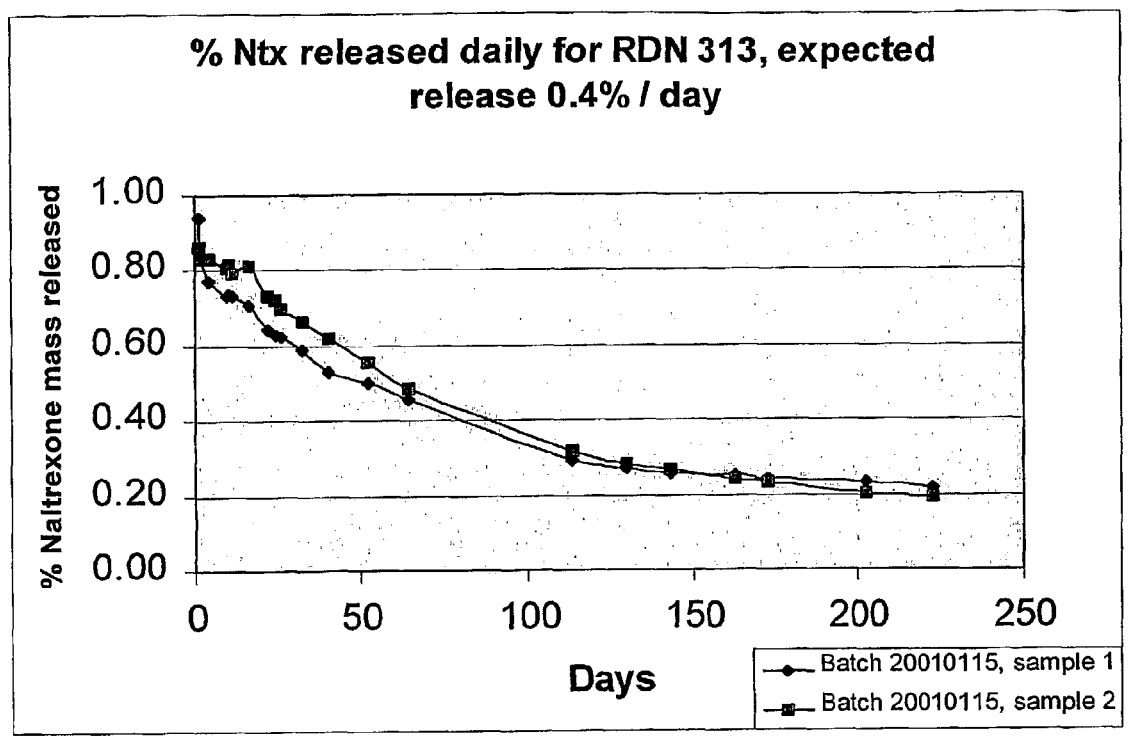
FIG. 13 shows release rates of naltrexone implants in a water bath expected to release 0.4% naltrexone per day. The graph shows that the implant releases naltrexone past 200 days and has at about 200 days only released 40-48% of the total mass of the implant.

FIG. 13 shows release rates of naltrexone implants in a water bath expected to release 0.4% naltrexone per day. The graph shows that the implant releases naltrexone past 200 days and has at about 200 days only released 40-48% of the total mass of the implant.

EXAMPLE 5

Delivery of Naltrexone

The following example illustrates 3 types of implants. These are implants releasing at 0.2% of its naltrexone mass per day, 0.4%/day and 0.8%/day all produced according to the present invention.

Figure 14:
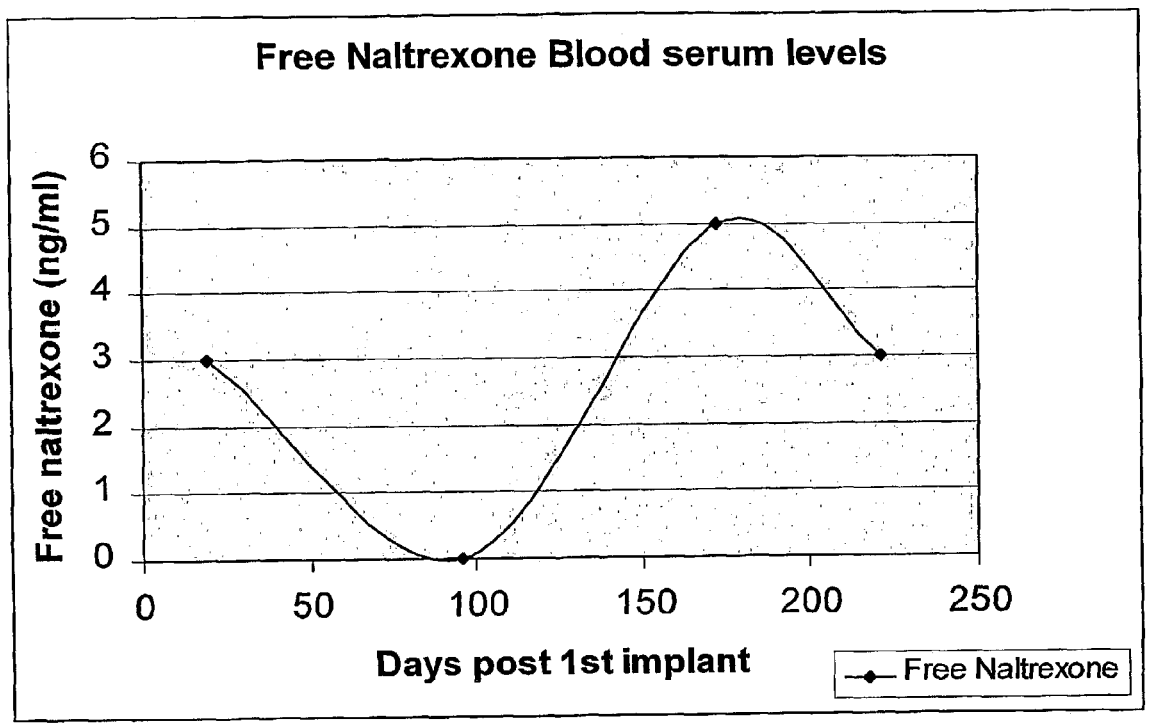
FIG. 14 shows free naltrexone blood serum levels of a patient administered with two implants, each containing 1.8 g of naltrexone expected to release 0.2% per day.

The slower the release rate, the longer the implant will last. Clinically, 0.2% per day implants don't really achieve high enough blood levels in the first 100 days to completely block cravings and heroin use, however after 100 days they start to release enough to block cravings and heroin use. This is best demonstrated by FIG. 14 from a patient who was implanted with 2×0.2%/day implants.

Figure 15:
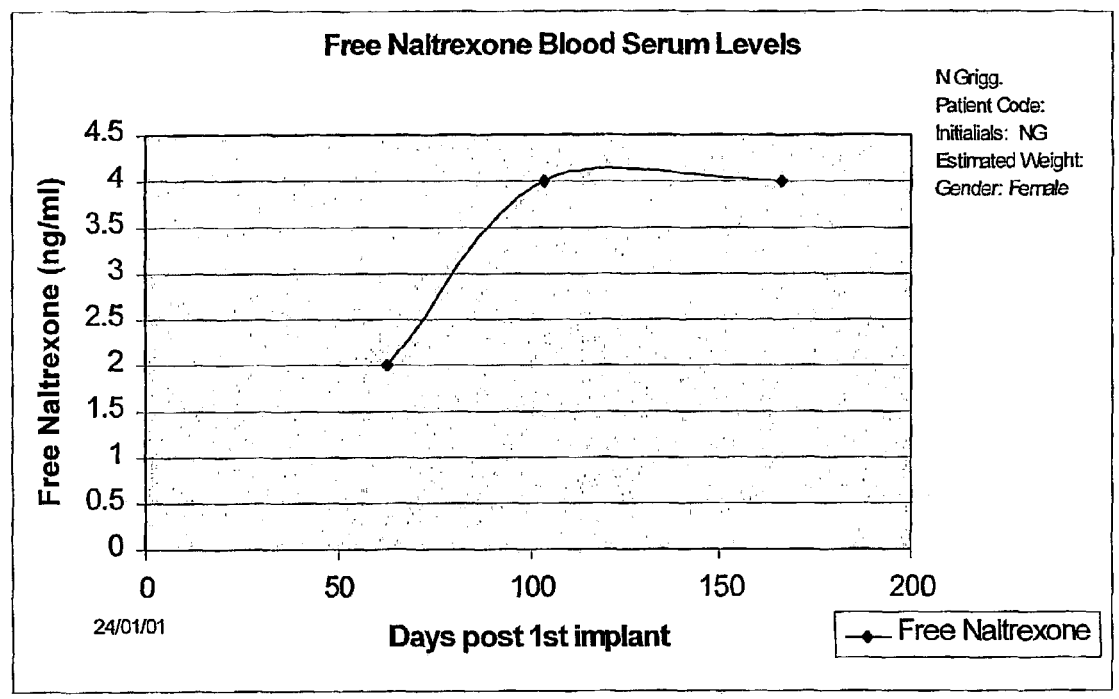
FIG. 15 shows free blood serum levels of a patient administered with two implants, each containing 1.8 g of naltrexone expected to release 0.4% per day.
Figure 16:
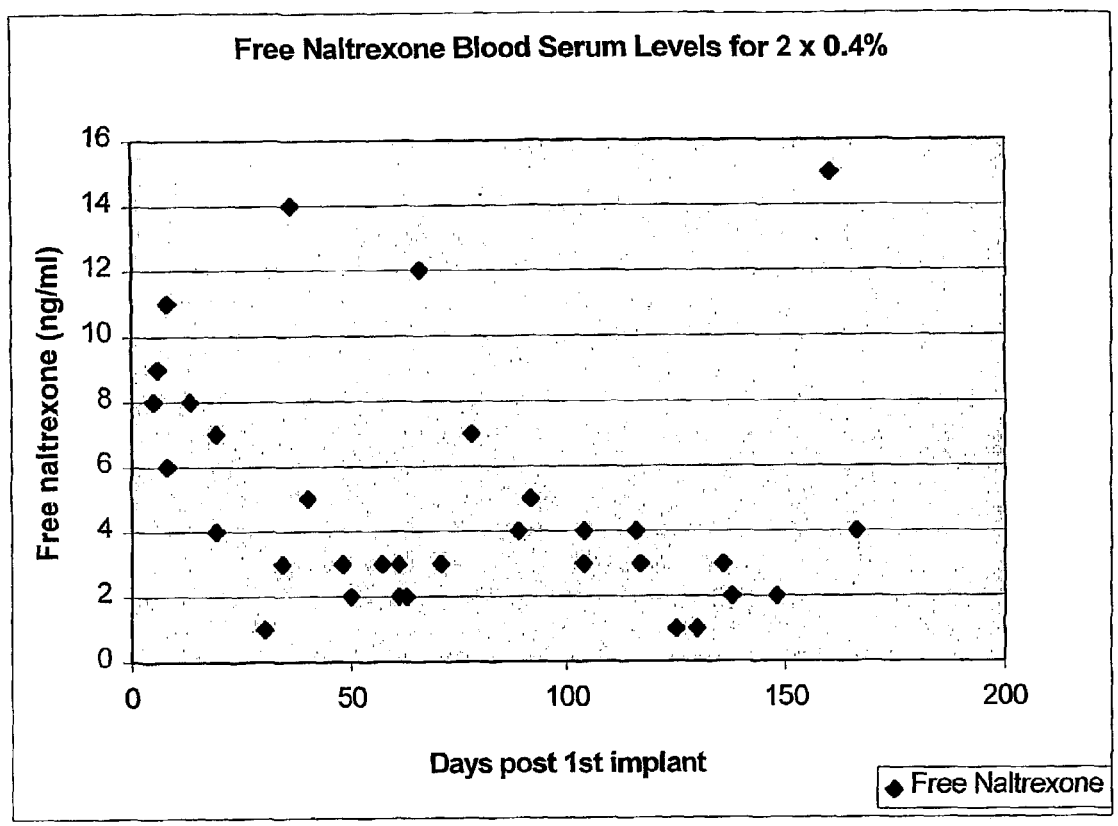
FIG. 16 shows free blood serum levels of approximately 11 patients each administered with 2 implants each containing 1.8 g naltrexone releasing at 0.4% per day.

Blood serum levels from patients implanted with 2×0.4%/day implants show good blood serum levels and therefore good coverage up to 130-150 days (and probably more however we only have data up to 166 days). These implants give good coverage in the first 100+days however you would expect them to run out quicker than the 0.2%/day implants as they have released more initially. This is illustrated by FIGS. 15 and 16.

Figure 17:
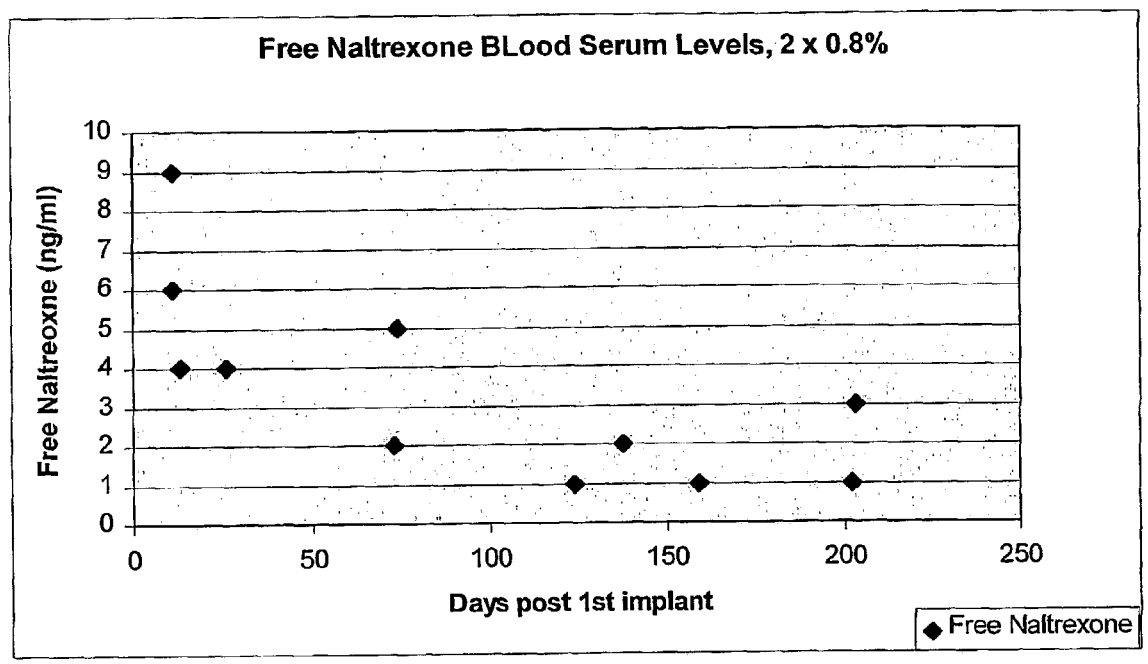
FIG. 17 shows free naltrexone blood levels of approximately 5 patients, each administered with 2 implants, each containing 1.8 g naltrexone expected to release 0.8% per day. This graph shows that the rate of naltrexone released is still steady at the 200 day mark.

Data from the 0.8%/day implants shows that good levels are achieved initially (as expected from the 0.4% data). One would expect the patients with 2×0.4%/day implants to also have good levels in excess of the 200+ day mark based on this and water bath data. This is highlighted by FIG. 17, which shows data from patients implanted with 2×0.8%/day implants with some patients registering good levels at the 200+ day mark.

EXAMPLE 6

Method of Administration of Implantable Naltrexone

Described below is an example of the present invention, wherein the implant is.

naltrexone. Preferably the diameter of a naltrexone implant ranges from 5 mm to 8 mm In FIG. 18 and FIG. 18a a needle 1 and sheath 2 are inserted into subcutaneous tissue 3 to make an incision 4 having the width of the needle 1 and sheath 2. Preferably, the diameter of the needle is 2 mm. Sheath 2 has a sheath hub 5 at the sheath proximal end and bore 6 adapted to receive needle 1. FIG. 18b shows the removal of needle 1 from the sheath 2, whilst keeping the sheath 2 inserted in the incision 4 and subcutaneous tissue. Needle 1 has a needle hub 7 at the needle proximal end.

Dilation of the opening of the incision 4 can be achieved by inserting a dilator 8 and sheath 9 of a diameter larger than that of the needle and sheath 2 into the bore 6 of sheath 2 and through sheath 2 such that sheath 2 is split into two pieces 10 and 11 as shown in FIGS. 18c, 18d and 18e. The two pieces 10 and 11 of sheath 2, remain in the subcutaneous tissue. Preferably, the diameter of dilator 8 is 4 mm. Dilator 8 is then removed from sheath 9, but sheath 9 remains in incision 4 and in the subcutaneous tissue 3.

Further dilation is required. Thus, in FIG. 18f, dilator 12 and sheath 13 of larger diameter than dilator 8 and sheath 9 are provided. Preferably, the diameter of dilator 12 is 6 mm.

Figure 18H:
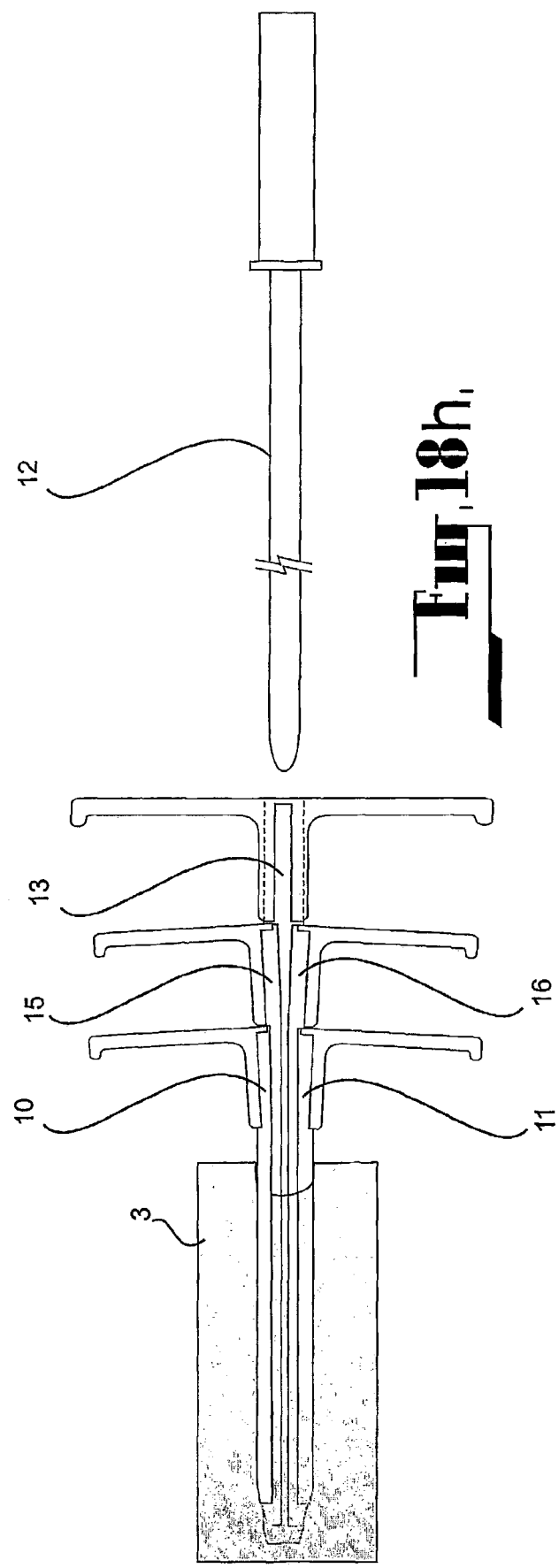

Further dilation of the opening of the incision 4 can be achieved by inserting a dilator 12 and sheath 13 of a diameter larger than that of sheath 8 through the bore 14 of sheath 8 such that sheath 8 is split into two pieces 15 and 16 as shown in FIGS. 18f and 18g. Preferably, the diameter of dilator 12 is 6 mm. Dilator 12 is then removed from sheath 13, but sheath 13 remains in the incision 4 and the subcutaneous tissue 3, as shown in FIG. 18h.

FIG. 19 shows that the opening of the incision is of a sufficient size to receive the implant(s). The last dilator 12 is removed, but the accompanying sheath 13 is left in the site. A sheath 17 of smaller diameter which can accommodate the implant(s) 18 and containing implant(s) is pushed through the bore 19 of sheath 13 which has been left in the site. The dilator 20 accompanying the sheath 17 containing the implant(s) is then used to push the implant(s) 18 through the bore 21 of sheath 17 into the subcutaneous tissue.

FIG. 20 shows a sheath containing implant(s).

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively, and any and all combinations or any two or more of the steps or features.

The invention claimed is:

1. A pharmaceutical implant adapted for sustained release of an active agent(s) over an extended period of time at a predetermined rate without an initial burst release of the agent(s) upon administration, wherein the implant comprises:
   (i) a coating prepared from one or more layers of a biodegradable polymer, which resists degradation for at least 30 days when positioned in situ in a patient, while allowing active agent to diffuse out of the implant during this period, and
   (ii) an inner portion comprising a plurality of micro-capsules containing at least the active agent(s), wherein the micro-capsules have been compressed into the form of a tablet to suppress the rate of release of the active agent(s) from the micro-capsules, wherein the active agent(s) comprises naltrexone.

2. The implant of claim 1 wherein the coating is 0.001 mm to 1 mm in thickness.

3. The implant of claim 2 wherein the coating is from 0.01 mm to 1 mm in thickness.

4. The implant of claim 3 wherein the coating is from 0.1 mm to 1 mm in thickness.

5. The implant of claim 1 wherein the diameter of the implant is between 3 mm to 12 mm.

6. The implant of claim 5 wherein the diameter of the implant is between 5 mm and 8 mm.

7. The implant of claim 6 wherein the height of the implant is between 3 mm and 15 mm.

8. The implant of claim 1 wherein the implant resists degradation for at least 45 days.

9. The implant of claim 8 wherein the implant resists degradation for at least 3 months.

10. The implant of claim 9 wherein the implant resists degradation for at least 1 year.

11. The implant of claim 1 wherein the coating is 0.001 mm to 1 mm in thickness, the implant diameter is between 3 mm to 12 mm, and the implant resists degradation for at least 45 days.

12. The implant of claim 1 wherein the coating is 0.001 mm to 1 mm in thickness, the implant diameter is between 5 mm to 8 mm, and the implant resists degradation for at least 3 months.

13. The implant of claim 12 wherein the coating layer is 0.1 mm to 1 mm in thickness, and the implant resists degradation for at least 1 year.

14. The implant of claim 1 wherein a force of at least 5 kg is required to fracture the surface of the implant.

15. The implant of claim 1 comprising a plurality of tablets comprising the active agent(s) and coated with at least one coating of biodegradable polymer.

16. The implant of claim 1 wherein the implant provides an effective dosage range of naltrexone of between about 1 g to about 20 g.

17. The implant of claim 16 wherein the dosage range is between about 3 g to about 15 g.

18. The implant of claim 17 wherein the dosage range is between 3.6 g to 7.2 g.

19. The implant of claim 16 wherein the delivery rate of naltrexone is between about 0.1 mg per day to 30 mg per day.

20. The implant of claim 19 wherein the delivery rate is between 1 mg per day to 5 mg per day.

21. The implant of claim 19 wherein the delivery rate is between 3.6 mg per day to 14.4 mg per day.

22. The implant of claim 1 wherein the size of the micro-capsules is between 30-100 microns.

23. The implant of claim 1 wherein the coating comprises two layers of polymer.

24. The implant of claim 1 wherein the coating comprises three layers of polymer.

25. The implant of claim 1 wherein the biodegradable polymer is selected from the group consisting of poly(glycolic acid), poly-D,L-lactic acid, poly-L-lactic acid, copolymers of the foregoing, poly(aliphatic carboxylic acids), copolyoxaates, polycaprolactone, polydioxonone, poly (ortho carbonates), poly(acetals), poly(lactic acid caprolactone), polyorthoesters, poly(glycolic acid-caprolactone), polyanhydrides, albumin, casein, and glycerol mono-and distearate.

26. A pharmaceutical implant adapted for sustained release of an active agent(s) over an extended period of time at a predetermined rate without an initial burst release of the agent(s) upon administration, wherein the implant comprises:
  (i) a coating prepared from one or more layers of a biodegradable polymer, which resists degradation for at least 30 days when positioned in situ in a patient, while allowing active agent to diffuse out of the implant during this period, and
  (ii) an inner portion comprising a plurality of micro-capsules containing at least the active agent(s), wherein the micro-capsules have been compressed into the form of a tablet to suppress the rate of release of the active agent(s) from the micro-capsules, wherein the active agent(s) comprises naltrexone, the coating is 0.001 mm to 1 mm in thickness, the diameter of the implant is between 3 mm to 12 mm, the implant resists degradation for at least 3 months, and provides an effective dosage range of naltrexone of between about 1 g to about 20 g, and the naltrexone delivery rate is between about 0.1 mg per day to 30 mg per day.

27. The implant of claim 1 wherein the implants comprise a plurality of tablets that each provide one or more different properties, respectively, selected from the group consisting of dimensions, degradation rate, effective dosage, delivery rate, and coating thickness.

28. The implant of claim 26 wherein the tablet coatings are independently between 0.01 mm to 1 mm in thickness.

29. The implant of claim 28 wherein the tablet coatings are independently between 0.1 mm to 1 mm in thickness.

30. The implant of claim 27 wherein at least one of the coated tablets resists degradation for at least 45 days.

31. The implant of claim 30 wherein at least one of the coated tablets resists degradation for at least 3 months.

32. The implant of claim 31 wherein at least one of the coated tablets resists degradation for at least 1 year.

33. The implant of claim 27 wherein at least one of the tablets provides an effective dosage range of naltrexone of between about 1 g to about 20 g.

34. The implant of claim 33 wherein the dosage range is between about 3 g to about 15 g.

35. The implant of claim 34 wherein the dosage range is between 3.6 g to 7.2 g.

36. The implant of claim 27 wherein at least one tablet provides a delivery rate of naltrexone of between about 0.1 mg per day to 30 mg per day.

37. The implant of claim 36 wherein the delivery rate is between 3.6 mg per day to 14.4 mg per day.

38. The implant of claim 27 wherein the coating of at least one tablet comprises two layers of polymer.

39. The implant of claim 27 wherein the coating of at least one tablet comprises three layers of polymer.

40. The implant of claim 27 wherein the biodegradable polymer is selected from the group consisting of poly(glycolic acid), poly-D,L-lactic acid, poly-L-lactic acid, copolymers of the foregoing, poly(aliphatic carboxylic acids), copolyoxaates, polycaprolactone, polydioxonone, poly (ortho carbonates), poly(acetals), poly(lactic acid caprolactone), polyorthoesters, poly(glycolic acid-caprolactone), polyanhydrides, albumin, casein, and glycerol mono-and distearate.

41. A method of treating a patient by administering a pharmaceutical implant adapted for sustained release of an active agent(s) over an extended period of time of at least 30 days at a therapeutic rate without an initial burst release of the agent(s) upon administration, wherein the implant comprises:
  (i) a coating prepared from one or more layers of a biodegradable polymer, which resists degradation for at least 30 days when positioned in situ in a patient, while allowing active agent to diffuse out of the implant during this period, and
  (ii) an inner portion comprising a plurality of micro-capsules containing at least the active agent(s), wherein the micro-capsules have been compressed into the form of a tablet to suppress the rate of release of the active agent(s) from the micro-capsules, wherein the active agent(s) comprises naltrexone.

42. The method of claim 41 wherein the coating is 0.001 mm to 1 mm in thickness.

43. The method of claim 42 wherein the coating is from 0.01 mm to 1 mm in thickness.

44. The method of claim 43 wherein the coating is from 0.1 mm to 1 mm in thickness.

45. The method of claim 41 wherein the diameter of the implant is between 3 mm to 12 mm.

46. The method of claim 45 wherein the diameter of the implant is between 5 mm and 8 mm.

47. The method of claim 45 wherein the height of the implant is between 3 mm and 15 mm.

48. The method of claim 41 wherein the implant resists degradation for at least 45 days.

49. The method of claim 48 wherein the implant resists degradation for at least 3 months.

50. The method of claim 49 wherein the implant resists degradation for at least 1 year.

51. The method of claim 41 wherein a force of at least 5 kg is required to fracture the surface of the implant.

52. The method of claim 41 comprising a plurality of tablets comprising the active agent(s) and coated with at least one coating of biodegradable polymer.

53. The method of claim 41 wherein the implant provides an effective dosage range of naltrexone of between about 1 g to about 20 g.

54. The method of claim 53 wherein the dosage range is between about 3 g to about 15 g.

55. The method of claim 54 wherein the dosage range is between 3.6 g to 7.2 g.

56. The method of claim 53 wherein the delivery rate of naltrexone is between about 0.1 mg per day to 30 mg per day.

57. The method of claim 56 wherein the delivery rate is between 1 mg per day to 5 mg per day.

58. The method of claim 56 wherein the delivery rate is between 3.6 mg per day to 14.4 mg per day.

59. The method of claim 41 wherein the coating comprises two layers of polymer.

60. The method of claim 41 wherein the coating comprises three layers of polymer.

61. The method of claim 41 wherein the biodegradable polymer is selected from the group consisting of poly(glycolic acid), poly-D,L-lactic acid, poly-L-lactic acid, copolymers of the foregoing, poly(aliphatic carboxylic acids), copolyoxaates, polycaprolactone, polydioxonone, poly(ortho carbonates), poly(acetals), poly(lactic acid caprolactone), polyorthoesters, poly(glycolic acid-caprolactone), polyanhydrides, albumin, casein, and glycerol mono-and distearate.

62. A method of treating a patient by administering a pharmaceutical implant adapted for sustained release of an active agent(s) over an extended period of time of at least 30 days at a therapeutic rate without an initial burst release of the agent(s) upon administration, wherein the implant comprises:
  (i) a coating prepared from one or more layers of a biodegradable polymer, which resists degradation for at least 30 days when positioned in situ in a patient, while allowing active agent to diffuse out of the implant during this period, and
  (ii) an inner portion comprising a plurality of micro-capsules containing at least the active agent(s), wherein the micro-capsules have been compressed into the form of a tablet to suppress the rate of release of the active agent(s) from the micro-capsules, wherein the active agent(s) comprises naltrexone, the coating is 0.001 mm to 1 mm in thickness, the diameter of the implant is between 3 mm to 12 mm, the implant resists degradation for at least 3 months, and provides an effective dosage range of naltrexone of between about 1 g to about 20 g and a delivery rate of naltrexone is between about 0.1 mg per day to 30 mg per day.

* * * * *